United States Patent
Wang et al.

(10) Patent No.: US 11,174,600 B2
(45) Date of Patent: *Nov. 16, 2021

(54) ARTIFICIAL TURF FILAMENT AND ARTICLES INCORPORATING SAME

(71) Applicant: Dow Global Technologies LLC, Midland, MI (US)

(72) Inventors: Jian Wang, Freeport, TX (US); Pradeep Jain, Lake Jackson, TX (US); Mehmet Demirors, Freeport, TX (US); Rajen M. Patel, Freeport, TX (US); Joseph L. Deavenport, Freeport, TX (US); David Lopez, Tarragona (ES)

(73) Assignee: Dow Global Technologies LLC, Midland, MI (US)

( * ) Notice: Subject to any disclaimer, the term of this patent is extended or adjusted under 35 U.S.C. 154(b) by 224 days.

This patent is subject to a terminal disclaimer.

(21) Appl. No.: 15/318,200

(22) PCT Filed: Jun. 26, 2015

(86) PCT No.: PCT/IB2015/001185
§ 371 (c)(1),
(2) Date: Feb. 2, 2017

(87) PCT Pub. No.: WO2015/198138
PCT Pub. Date: Dec. 30, 2015

(65) Prior Publication Data
US 2017/0226332 A1    Aug. 10, 2017

Related U.S. Application Data

(60) Provisional application No. 62/017,525, filed on Jun. 26, 2014.

(51) Int. Cl.
*E01C 13/08*    (2006.01)
*C08J 5/18*    (2006.01)
(Continued)

(52) U.S. Cl.
CPC ........ *E01C 13/08* (2013.01); *A61F 13/51401* (2013.01); *A61F 13/51458* (2013.01);
(Continued)

(58) Field of Classification Search
CPC ............ E01C 13/08; Y10T 428/23993; D06N 7/0065; D06N 2201/0254; C08L 23/0815;
(Continued)

(56) References Cited

U.S. PATENT DOCUMENTS 3,645,992 A * 2/1972 Elston .................. C08F 210/16
526/169.2
4,314,912 A    2/1982 Lowery, Jr. et al.
(Continued)

FOREIGN PATENT DOCUMENTS

CN    103174081 A    6/2013
EP    2752509 A1    7/2014
(Continued)

OTHER PUBLICATIONS

Karjala, Annual Technical Conference—Society of Plastics Engineers, 2008, p. 887-891.
(Continued)

*Primary Examiner* — Cheryl Juska

(57) ABSTRACT

Artificial turf filaments formed from polyethylene are provided that can have desirable properties. In one aspect, an artificial turf filament comprises a composition comprising a first composition, wherein the first composition comprises at least one ethylene-based polymer and wherein the first composition comprises a MWCDI value greater than 0.9, and a melt index ratio (I10/I2) that meets the following equation: I10/I2≥7.0−1.2×log (I2).

13 Claims, 6 Drawing Sheets

(51) Int. Cl.

| | |
|---|---|
| *C08L 23/08* | (2006.01) |
| *D02G 3/44* | (2006.01) |
| *D01F 6/46* | (2006.01) |
| *D06N 7/00* | (2006.01) |
| *C08F 210/16* | (2006.01) |
| *C08J 5/00* | (2006.01) |
| *B32B 5/00* | (2006.01) |
| *B32B 5/02* | (2006.01) |
| *B32B 7/00* | (2019.01) |
| *B32B 7/02* | (2019.01) |
| *B32B 27/06* | (2006.01) |
| *B32B 27/18* | (2006.01) |
| *B32B 27/20* | (2006.01) |
| *B32B 27/28* | (2006.01) |
| *B32B 27/30* | (2006.01) |
| *B32B 27/32* | (2006.01) |
| *D02G 3/02* | (2006.01) |
| *A61F 13/514* | (2006.01) |
| *B32B 27/08* | (2006.01) |
| *B32B 27/12* | (2006.01) |
| *C08K 3/26* | (2006.01) |

(52) U.S. Cl.
CPC .............. *B32B 5/00* (2013.01); *B32B 5/02* (2013.01); *B32B 5/022* (2013.01); *B32B 7/00* (2013.01); *B32B 7/02* (2013.01); *B32B 27/06* (2013.01); *B32B 27/08* (2013.01); *B32B 27/12* (2013.01); *B32B 27/18* (2013.01); *B32B 27/20* (2013.01); *B32B 27/28* (2013.01); *B32B 27/30* (2013.01); *B32B 27/306* (2013.01); *B32B 27/308* (2013.01); *B32B 27/32* (2013.01); *B32B 27/325* (2013.01); *C08F 210/16* (2013.01); *C08J 5/00* (2013.01); *C08J 5/18* (2013.01); *C08K 3/26* (2013.01); *C08L 23/0807* (2013.01); *C08L 23/0815* (2013.01); *D01F 6/46* (2013.01); *D02G 3/02* (2013.01); *D02G 3/44* (2013.01); *D06N 7/0065* (2013.01); *A61F 2013/51409* (2013.01); *B32B 2255/00* (2013.01); *B32B 2255/02* (2013.01); *B32B 2262/00* (2013.01); *B32B 2262/02* (2013.01); *B32B 2262/0253* (2013.01); *B32B 2270/00* (2013.01); *B32B 2307/50* (2013.01); *B32B 2307/514* (2013.01); *B32B 2307/544* (2013.01); *B32B 2307/718* (2013.01); *B32B 2307/724* (2013.01); *B32B 2307/726* (2013.01); *B32B 2555/00* (2013.01); *C08F 2500/11* (2013.01); *C08F 2500/12* (2013.01); *C08F 2500/18* (2013.01); *C08J 2323/06* (2013.01); *C08J 2323/08* (2013.01); *C08J 2423/08* (2013.01); *C08K 2003/265* (2013.01); *C08L 2203/12* (2013.01); *C08L 2205/025* (2013.01); *C08L 2205/16* (2013.01); *C08L 2314/02* (2013.01); *C08L 2314/06* (2013.01); *D06N 2201/0254* (2013.01); *D10B 2505/202* (2013.01); *Y10T 428/23993* (2015.04)

(58) Field of Classification Search
CPC ............ C08L 23/0807; C08L 2314/02; C08L 2314/06; C08L 2205/16; C08L 2203/12; C08L 2423/08; C08L 2323/08; C08J 5/00; C08J 2323/06; B32B 27/06; B32B 27/08; B32B 27/12; B32B 27/32; B32B 27/325; B32B 27/327; B32B 5/00; B32B 5/02; B32B 7/00; B32B 7/02; B32B 33/00; C08F 210/16; C08F 2500/12; D10B 2505/202; D02G 3/02; D02G 3/44
See application file for complete search history.

(56) References Cited

U.S. PATENT DOCUMENTS

| | | | |
|---|---|---|---|
| 4,547,475 | A | 10/1985 | Glass et al. |
| 4,612,300 | A | 9/1986 | Coleman, III |
| 5,064,802 | A | 11/1991 | Stevens et al. |
| 5,153,157 | A | 10/1992 | Hlatky et al. |
| 5,296,433 | A | 3/1994 | Siedle et al. |
| 5,321,106 | A | 6/1994 | LaPointe |
| 5,350,723 | A | 9/1994 | Neithamer et al. |
| 5,425,872 | A | 6/1995 | Devore et al. |
| 5,601,886 | A † | 2/1997 | Ishikawa |
| 5,625,087 | A | 4/1997 | Devore et al. |
| 5,721,185 | A | 2/1998 | LaPointe et al. |
| 5,783,512 | A | 7/1998 | Jacobsen et al. |
| 5,883,204 | A | 3/1999 | Spencer et al. |
| 5,919,983 | A | 7/1999 | Rosen et al. |
| 5,977,251 | A | 11/1999 | Kao et al. |
| 6,103,657 | A | 8/2000 | Murray |
| 6,515,155 | B1 | 2/2003 | Klosin et al. |
| 6,691,455 | B1 † | 2/2004 | Bergevin |
| 6,696,379 | B1 | 2/2004 | Carnahan et al. |
| 6,908,968 | B2 † | 6/2005 | Jain |
| 7,163,907 | B1 | 1/2007 | Canich et al. |
| 7,199,203 | B2 | 4/2007 | Stevens et al. |
| 7,596,433 | B2 | 9/2009 | Muinonen et al. |
| 7,915,356 | B2 * | 3/2011 | Arcella ............... B01F 7/00975 264/238 |
| 8,038,436 | B2 † | 10/2011 | Rogers |
| 8,821,995 | B2 | 9/2014 | Chai et al. |
| 10,138,362 | B2 * | 11/2018 | Wang ..................... B32B 5/02 |
| 2009/0306299 | A1 * | 12/2009 | Kipke .................... C08F 10/00 525/240 |
| 2010/0304052 | A1 † | 12/2010 | Chai |
| 2013/0030123 | A1 * | 1/2013 | Martin ..................... D01F 6/46 525/95 |
| 2013/0046061 | A1 | 2/2013 | Hermel-Davidock et al. |
| 2013/0080208 | A1 | 3/2013 | Wang et al. |
| 2014/0242304 | A1 | 8/2014 | Sandkuehler et al. |
| 2014/0248811 | A1 * | 9/2014 | Degroot ..................... B32B 5/24 442/170 |
| 2014/0248816 | A1 | 9/2014 | Bonavoglia et al. |
| 2015/0204027 | A1 | 7/2015 | Bonavoglia et al. |
| 2015/0225520 | A1 * | 8/2015 | Bensason .................. C08J 5/18 526/348.1 |
| 2015/0259586 | A1 * | 9/2015 | Kapur .................... C08F 210/16 428/476.9 |
| 2016/0017518 | A1 * | 1/2016 | Lorenzo .................... D04H 3/16 442/334 |
| 2017/0081444 | A1 * | 3/2017 | Wang ..................... E01C 13/08 |
| 2017/0129229 | A1 * | 5/2017 | Wang ..................... B32B 27/06 |
| 2017/0129230 | A1 * | 5/2017 | Wang ..................... C08L 23/0815 |
| 2017/0152377 | A1 * | 6/2017 | Wang ..................... C08F 210/16 |

FOREIGN PATENT DOCUMENTS

| | | | |
|---|---|---|---|
| EP | 3054038 | A1 | 8/2016 |
| WO | 98/21274 | † | 5/1998 |
| WO | 2009005375 | A1 | 1/2009 |
| WO | WO-2011126886 | A1 * | 10/2011 ............... D01F 6/46 |
| WO | 2012/134700 | † | 10/2012 |
| WO | 2013052636 | A1 | 4/2013 |
| WO | 2014012250 | A1 | 1/2014 |
| WO | 2014/058639 | † | 4/2014 |
| WO | 2015200740 | A2 | 12/2015 |
| WO | 2015200741 | A1 | 12/2015 |

(56) References Cited

FOREIGN PATENT DOCUMENTS

| | | |
|---|---|---|
| WO | 2015200742 A1 | 12/2015 |
| WO | 2015200743 A1 | 12/2015 |

OTHER PUBLICATIONS

PCT/IB2015/001185, International Search Report and Written Opinion with a dated Sep. 26, 2015.

PCT/IB2015/001185, International Preliminary Report on Patentability with a dated Jan. 5, 2017.

Karjala et al., "Detection of Low Levels of Long-Chain Branching in Polyolefins", ANTEC, (2008), pp. 887-891.†

Monrabal et al., "Crystallization Elution Fractionation and Thermal Gradient Interaction Chromatography. Techniques Comparison", Macromol. Symp., vol. 312 (2012), pp. 115-129.†

\* cited by examiner
† cited by third party

ARTIFICIAL TURF FILAMENT AND ARTICLES INCORPORATING SAME

FIELD

The present invention relates generally to artificial turf filaments, articles incorporating turf filaments, and their manufacture.

INTRODUCTION

Synthetic or artificial turfs are increasingly being used as an alternative to natural grass turf for use on sport athletic fields, playgrounds, landscaping, and in other leisure applications. To produce an artificial turf, turf yarns may be extruded, and then tufted through a primary backing. A secondary backing may be applied to "glue" the turf yarn to the primary backing. The extruded turf yarns may have different yarn profiles. That is, various turf yarn cross-sectional shapes and/or thicknesses may be used, which can have a strong impact on the optical appearance of the yarns as well as on their performance during the assembly process and life of the artificial turf. While ethylene-based polymers have been used for artificial turf filaments, there remains a need for ethylene-based compositions that can be used to in the manufacture of artificial turf filaments having desirable properties and related articles.

SUMMARY

The present invention utilizes ethylene-based polymers exhibiting certain features in the formation of artificial turf filaments with desirable properties. For example, in some embodiments, the artificial turf filaments provide desirable tenacity, elongation, shrinkage, and/or curl.

In one aspect, the present invention provides an artificial turf filament comprising a first composition, wherein the first composition comprises at least one ethylene-based polymer and wherein the first composition comprises a MWCDI value greater than 0.9, and a melt index ratio (I10/I2) that meets the following equation: $I10/I2 \geq 7.0 - 1.2 \times \log(I2)$.

These and other embodiments are described in more detail in the Detailed Description.

DETAILED DESCRIPTION

Figure 1:
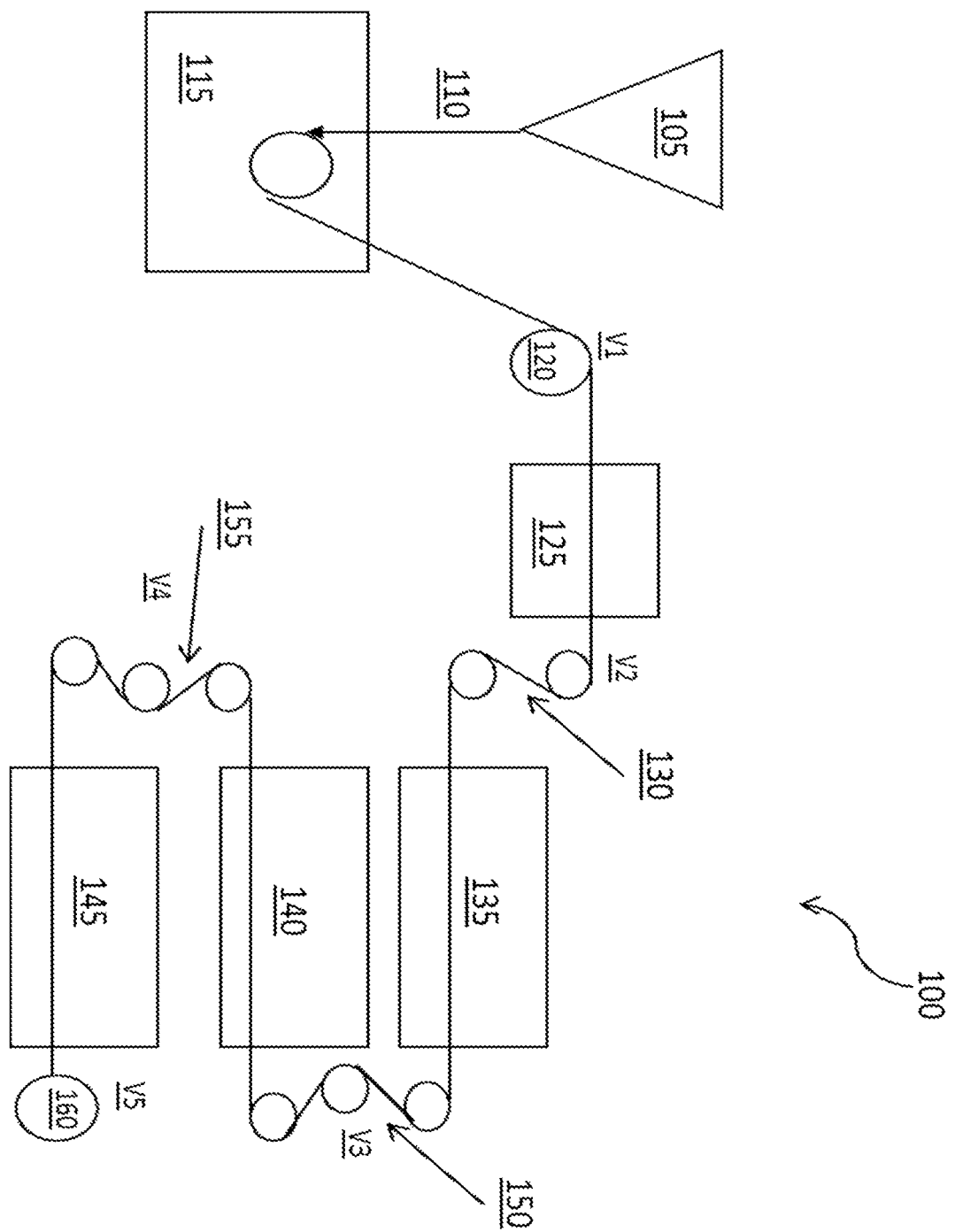
FIG. 1 pictorially depicts an exemplary monofilament extrusion line that may be used to produce the inventive and comparative artificial turf filaments.

It has been discovered that the inventive compositions can be used to form inventive artificial turf filaments and related products. Such compositions contain an ethylene-based polymer that has a superior comonomer distribution, which is significantly higher in comonomer concentration, and a good distribution of comonomer, in the high molecular weight polymer molecules, and is significantly lower in comonomer concentration in the low molecular weight polymer molecules, as compared to conventional polymers of the art at the same overall density. It has also been discovered that the ethylene-based polymer has low LCB (Long Chain Branches), as indicated by low ZSVR, as compared to conventional polymers. As a result of this optimized distribution of the comonomer, as well as the inherent low LCB nature, the inventive compositions have more tie chains, and thus, improved film toughness. The inventive compositions can be useful in forming the inventive artificial turf filaments and related products of the present invention.

The invention provides a composition comprising a first composition, comprising at least one ethylene-based polymer, wherein the first composition comprises a MWCDI value greater than 0.9, and a melt index ratio (I10/I2) that meets the following equation: $I10/I2 \geq 7.0 - 1.2 \times \log(I2)$.

The inventive composition may comprise a combination of two or more embodiments described herein.

The first composition may comprise a combination of two or more embodiments as described herein.

The ethylene-based polymer may comprise a combination of two or more embodiments as described herein.

In one embodiment, the first composition has a MWCDI value less than, or equal to, 10.0, further less than, or equal to, 8.0, further less than, or equal to, 6.0.

In one embodiment, the first composition has a MWCDI value less than, or equal to, 5.0, further less than, or equal to, 4.0, further less than, or equal to, 3.0.

In one embodiment, the first composition has a MWCDI value greater than, or equal to, 1.0, further greater than, or equal to, 1.1, further greater than, or equal to, 1.2.

In one embodiment, the first composition has a MWCDI value greater than, or equal to, 1.3, further greater than, or equal to, 1.4, further greater than, or equal to, 1.5.

In one embodiment, the first composition has a melt index ratio I10/I2 greater than, or equal to, 7.0, further greater than, or equal to, 7.1, further greater than, or equal to, 7.2, further greater than, or equal to, 7.3.

In one embodiment, the first composition has a melt index ratio I10/I2 less than, or equal to, 9.2, further less than, or equal to, 9.0, further less than, or equal to, 8.8, further less than, or equal to, 8.5.

In one embodiment, the first composition has a ZSVR value from 1.2 to 3.0, further from 1.2 to 2.5, further 1.2 to 2.0.

In one embodiment, the first composition has a vinyl unsaturation level greater than 10 vinyls per 1,000,000 total carbons. For example, greater than 20 vinyls per 1,000,000 total carbons, or greater than 50 vinyls per 1,000,000 total carbons, or greater than 70 vinyls per 1,000,000 total carbons, or greater than 100 vinyls per 1,000,000 total carbons.

In one embodiment, the first composition has a density in the range of 0.910 to 0.940 g/cm³, for example from 0.910 to 0.930, or from 0.910 to 0.925 g/cm³. For example, the density can be from a lower limit of 0.910, 0.912, or 0.914 g/cm³, to an upper limit of 0.925, 0.927, or 0.930 g/cm³ (1 cm³=1 cc).

In one embodiment, the first composition has a melt index ($I_2$ or I2; at 190° C./2.16 kg) from 0.1 to 50 g/10 minutes, for example from 0.1 to 30 g/10 minutes, or from 0.1 to 20 g/10 minutes, or from 0.1 to 10 g/10 minutes. For example, the melt index ($I_2$ or I2; at 190° C./2.16 kg) can be from a lower limit of 0.1, 0.2, or 0.5 g/10 minutes, to an upper limit of 1.0, 2.0, 3.0, 4.0, 5.0, 10, 15, 20, 25, 30, 40, or 50 g/10 minutes.

In one embodiment, the first composition has a molecular weight distribution, expressed as the ratio of the weight average molecular weight to number average molecular weight ($M_w/M_n$; as determined by cony. GPC) in the range of from 2.2 to 5.0. For example, the molecular weight distribution ($M_w/M_n$) can be from a lower limit of 2.2, 2.3, 2.4, 2.5, 3.0, 3.2, or 3.4, to an upper limit of 3.9, 4.0, 4.1, 4.2, 4.5, or 5.0.

In one embodiment, the first composition has a number average molecular weight ($M_n$; as determined by cony. GPC) in the range from 10,000 to 50,000 g/mole. For example, the number average molecular weight can be from a lower limit of 10,000, 20,000, or 25,000 g/mole, to an upper limit of 35,000, 40,000, 45,000, or 50,000 g/mole.

In one embodiment, the first composition has a weight average molecular weight ($M_w$; as determined by cony. GPC) in the range from 70,000 to 200,000 g/mole. For example, the number average molecular weight can be from a lower limit of 70,000, 75,000, or 78,000 g/mole, to an upper limit of 120,000, 140,000, 160,000, 180,000 or 200,000 g/mole.

In one embodiment, the first composition has a melt viscosity ratio, Eta*0.1/Eta*100, in the range from 2.2 to 7.0. For example, the number average molecular weight can be from a lower limit of 2.2, 2.3, 2.4 or 2.5, to an upper limit of 6.0, 6.2, 6.5, or 7.0.

In one embodiment, the ethylene-based polymer is an ethylene/α-olefin interpolymer, and further an ethylene/α-olefin copolymer.

In one embodiment, the first ethylene-based polymer is an ethylene/α-olefin interpolymer, and further an ethylene/α-olefin copolymer.

In one embodiment, the α-olefin has less than, or equal to, 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-butene, 1-hexene and 1-octene, and further 1-hexene and 1-octene.

In one embodiment, the ethylene-based polymer, or first ethylene-based polymer, has a molecular weight distribution ($M_w/M_n$; as determined by cony. GPC) in the range from 1.5 to 4.0, for example, from 1.5 to 3.5, or from 2.0 to 3.0. For example, the molecular weight distribution ($M_w/M_n$) can be from a lower limit of 1.5, 1.7, 2.0, 2.1, or 2.2, to an upper limit of 2.5, 2.6, 2.8, 3.0, 3.5 or 4.0.

In one embodiment, the first composition further comprises a second ethylene-based polymer. In a further embodiment, the second ethylene-based polymer is an ethylene/α-olefin interpolymer, and further an ethylene/α-olefin copolymer, or a LDPE.

In one embodiment, the α-olefin has less than, or equal to, 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-butene, 1-hexene and 1-octene, and further 1-hexene and 1-octene.

In one embodiment, the second ethylene-based polymer is a heterogeneously branched ethylene/α-olefin interpolymer, and further a heterogeneously branched ethylene/α-olefin copolymer. Heterogeneously branched ethylene/α-olefin interpolymers and copolymers are typically produced using Ziegler/Natta type catalyst system, and have more comonomer distributed in the lower molecular weight molecules of the polymer.

In one embodiment, the second ethylene-based polymer has a molecular weight distribution ($M_w/M_n$) in the range from 3.0 to 5.0, for example from 3.2 to 4.6. For example, the molecular weight distribution ($M_w/M_n$) can be from a lower limit of 3.2, 3.3, 3.5, 3.7, or 3.9, to an upper limit of 4.6, 4.7, 4.8, 4.9, or 5.0.

In one embodiment, the composition comprises from 50 to 80 wt %, or from 50 to 85 wt %, or from 50 to 90 wt %, or from 50 to 95 wt % of the first composition, based on the weight of the composition.

In one embodiment, the composition comprises greater than or equal to 80 wt %, or greater than or equal to 85 wt %, or greater than or equal to 90 wt %, or greater than or equal to 95 wt %, or greater than or equal to 98 wt % of the first composition, based on the weight of the composition.

In one embodiment, the composition further comprises another polymer. In a further embodiment, the polymer is selected from the following: a LLDPE, a VLDPE (a very low density polyethylene), a MDPE, a LDPE, a HDPE, a HMWHDPE (a high molecular weight HDPE), a propylene-based polymer, a polyolefin plastomer, a polyolefin elastomer, an olefin block copolymer, an ethylene vinyl acetate, an ethylene acrylic acid, an ethylene methacrylic acid, an ethylene methyl acrylate, an ethylene ethyl acrylate, an ethylene butyl acrylate, a polyisobutylene, a maleic anhydride-grafted polyolefin, an ionomer of any of the foregoing, or a combination thereof.

In one embodiment, the composition further comprises a LDPE. In a further embodiment, the LDPE is present in an amount from 5 to 50 wt %, further from 10 to 40 wt %, further from 15 to 30 wt %, based on the weight of the composition. In a further embodiment, the LDPE has a density from 0.915 to 0.930 g/cc, and a melt index (I2) from 0.15 to 30 g/10 min, further from 0.25 to 20 g/10 min.

In one embodiment, the composition further comprises one or more additives.

The invention also provides an article comprising at least one component formed from an inventive composition as described herein.

In some embodiments, the present invention relates to an artificial turf filament formed from any of the inventive compositions as described herein. In some embodiments, the first composition used in the artificial turf filament has a density of 0.905 to 0.940 g/cm³ and/or a melt index (I2) of 0.5 to 5 g/10 minutes. The first composition used in the artificial turf filament, in some embodiments, has a density of 0.918 to 0.935 g/cm³. In some embodiments, the artificial turf filament exhibits a shrink of less than 6.0%.

Some embodiments of the present invention relate to methods of manufacturing an artificial turf filament. A method of manufacturing an artificial turf filament, in some embodiments, comprises providing any of the inventive compositions described herein, and extruding the inventive composition into an artificial turf filament. In some embodiments, such methods further comprise stretching the artificial turf filament to a predetermined stretch ratio. The stretch ratio, in some embodiments, is at least 4. Artificial turf filaments can be stretched using cold drawing techniques, hot drawing techniques, or combinations thereof.

Some embodiments of the present invention relate to artificial turf. Artificial turf, according to some embodiments of the present invention, comprises a primary backing having a top side and a bottom side, and at least one artificial turf filament formed from any of the inventive compositions described herein, wherein the at least one artificial turf filament is affixed to the primary backing such that the at least one artificial turf filament provides a tufted face extending outwardly from the top side of the primary backing. In some embodiments, the artificial turf further comprises a secondary backing bonded to at least a portion of the bottom side of the primary backing such that the at least one artificial turf filament is affixed in place to the bottom side of the primary backing.

Some embodiments of the present invention relate to methods of manufacturing an artificial turf. A method of manufacturing an artificial turf, in some embodiments, comprises providing at least one artificial turf filament formed from any of the inventive compositions described herein, and affixing the at least one artificial turf filament to a primary backing such that that at least one artificial turf filament provides a tufted face extending outwardly from a top side of the primary backing. In some embodiments, such methods further comprise bonding a secondary backing to at least a portion of the bottom side of the primary backing such that the at least one artificial turf filament is affixed in place to the bottom side of the primary backing.

Polymerization

Polymerization processes include, but are not limited to, solution polymerization processes, using one or more conventional reactors, e.g., loop reactors, isothermal reactors, adiabatic reactors, stirred tank reactors, autoclave reactors in parallel, series, and/or any combinations thereof. The ethylene based polymer compositions of the present invention may, for example, be produced via solution phase polymerization processes, using one or more loop reactors, adiabatic reactors, and combinations thereof.

In general, the solution phase polymerization process occurs in one or more well mixed reactors, such as one or more loop reactors and/or one or more adiabatic reactors at a temperature in the range from 115 to 250° C.; for example, from 135 to 200° C., and at pressures in the range of from 300 to 1000 psig, for example, from 450 to 750 psig.

In one embodiment, the ethylene based polymer composition (e.g., the first composition recited in claim 1 or the first composition recited in claim 5) may be produced in two loop reactors in series configuration, the first reactor temperature is in the range from 115 to 200° C., for example, from 135 to 165° C., and the second reactor temperature is in the range from 150 to 210° C., for example, from 185 to 200° C. In another embodiment, the ethylene based polymer composition may be produced in a single reactor, the reactor temperature is in the range from 115 to 200° C., for example from 130 to 190° C. The residence time in a solution phase polymerization process is typically in the range from 2 to 40 minutes, for example from 5 to 20 minutes. Ethylene, solvent, one or more catalyst systems, optionally one or more cocatalysts, and optionally one or more comonomers, are fed continuously to one or more reactors. Exemplary solvents include, but are not limited to, isoparaffins. For example, such solvents are commercially available under the name ISOPAR E from ExxonMobil Chemical. The resultant mixture of the ethylene based polymer composition and solvent is then removed from the reactor or reactors, and the ethylene based polymer composition is isolated. Solvent is typically recovered via a solvent recovery unit, i.e., heat exchangers and separator vessel, and the solvent is then recycled back into the polymerization system.

In one embodiment, the ethylene based polymer composition may be produced, via a solution polymerization process, in a dual reactor system, for example a dual loop reactor system, wherein ethylene, and optionally one or more α-olefins, are polymerized in the presence of one or more catalyst systems, in one reactor, to produce a first ethylene-based polymer, and ethylene, and optionally one or more α-olefins, are polymerized in the presence of one or more catalyst systems, in a second reactor, to produce a second ethylene-based polymer. Additionally, one or more cocatalysts may be present.

In another embodiment, the ethylene based polymer composition may be produced via a solution polymerization process, in a single reactor system, for example, a single loop reactor system, wherein ethylene, and optionally one or more α-olefins, are polymerized in the presence of one or more catalyst systems. Additionally, one or more cocatalysts may be present.

As discussed above, the invention provides a process to form a composition comprising at least two ethylene-based polymers, said process comprising the following:

polymerizing ethylene, and optionally at least one comonomer, in solution, in the present of a catalyst system comprising a metal-ligand complex of Structure I, to form a first ethylene-based polymer; and polymerizing ethylene, and optionally at least one comonomer, in the presence of a catalyst system comprising a Ziegler/Natta catalyst, to form a second ethylene-based polymer; and wherein Structure I is as follows:

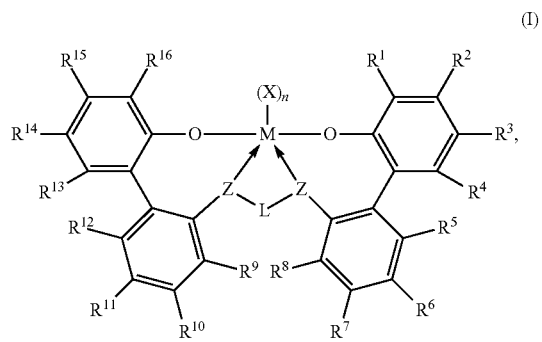

(I)

wherein:

M is titanium, zirconium, or hafnium, each, independently, being in a formal oxidation state of +2, +3, or +4; and n is an integer from 0 to 3, and wherein when n is 0, X is absent; and each X, independently, is a monodentate ligand that is neutral, monoanionic, or dianionic; or two Xs are taken together to form a bidentate ligand that is neutral, monoanionic, or dianionic; and X and n are chosen, in such a way, that the metal-ligand complex of formula (I) is, overall, neutral; and each Z, independently, is O, S, N($C_1$-$C_{40}$)hydrocarbyl, or P($C_1$-$C_{40}$)hydrocarbyl; and wherein the Z-L-Z fragment is comprised of formula (1):

(1)

$R^1$ through $R^{16}$ are each, independently, selected from the group consisting of the following: a substituted or unsubstituted ($C_1$-$C_{40}$)hydrocarbyl, a substituted or unsubstituted ($C_1$-$C_{40}$)heterohydrocarbyl, $Si(R^C)_3$, $Ge(R^C)_3$, $P(R^P)_2$, $N(R^N)_2$, $OR^C$, $SR^C$, $NO_2$, $CN$, $CF_3$, $R^CS(O)$—, $R^CS(O)_2$—, $(R^C)_2C=N$—, $R^CC(O)O$—, $R^COC(O)$—, $R^CC(O)N(R)$—, $(R^C)_2NC(O)$—, halogen atom, hydrogen atom; and wherein each $R^C$ is independently a (C1-C30)hydrocarbyl; $R^P$ is a (C1-C30)hydrocarbyl; and $R^N$ is a (C1-C30)hydrocarbyl; and wherein, optionally, two or more R groups (from $R^1$ through $R^{16}$) can combine together into one or more ring structures, with such ring structures each, independently, having from 3 to 50 atoms in the ring, excluding any hydrogen atom.

An inventive process may comprise a combination of two or more embodiments as described herein.

In one embodiment, said process comprises polymerizing ethylene, and optionally at least one α-olefin, in solution, in the presence of a catalyst system comprising a metal-ligand complex of Structure I, to form a first ethylene-based polymer; and polymerizing ethylene, and optionally at least one α-olefin, in the presence of a catalyst system comprising a Ziegler/Natta catalyst, to form a second ethylene-based polymer. In a further embodiment, each α-olefin is independently a C1-C8 α-olefin.

In one embodiment, optionally, two or more R groups from $R^9$ through $R^{13}$, or $R^4$ through $R^8$ can combine together into one or more ring structures, with such ring structures each, independently, having from 3 to 50 atoms in the ring, excluding any hydrogen atom.

In one embodiment, M is hafnium.

In one embodiment, $R^3$ and $R^{14}$ are each independently an alkyl, and further a C1-C3 alkyl, and further methyl.

In one embodiment, $R^1$ and $R^{16}$ are each as follows:

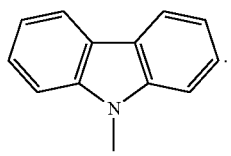

In one embodiment, each of the aryl, heteroaryl, hydrocarbyl, heterohydrocarbyl, $Si(R^C)_3$, $Ge(R^C)_3$, $P(R^P)_2$, $N(R^N)_2$, $OR^C$, $SR^C$, $R^CS(O)$—, $R^CS(O)_2$—, $(R^C)_2C=N$—, $R^CC(O)O$—, $R^COC(O)$—, $R^CC(O)N(R)$—, $(R^C)_2NC(O)$—, hydrocarbylene, and heterohydrocarbylene groups, independently, is unsubstituted or substituted with one or more $R^S$ substituents; and each $R^S$ independently is a halogen atom, polyfluoro substitution, perfluoro substitution, unsubstituted ($C_1$-$C_{18}$)alkyl, $F_3C$—, $FCH_2O$—, $F_2HCO$—, $F_3CO$—, $R_3Si$—, $R_3Ge$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, or $R_2NC(O)$—, or two of the $R^S$ are taken together to form an unsubstituted ($C_1$-$C_{18}$)alkylene, wherein each R independently is an unsubstituted ($C_1$-$C_{18}$)alkyl.

In one embodiment, two or more of $R^1$ through $R^{16}$ do not combine to form one or more ring structures.

In one embodiment, the catalyst system suitable for producing the first ethylene/α-olefin interpolymer is a catalyst system comprising bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following Structure: IA:

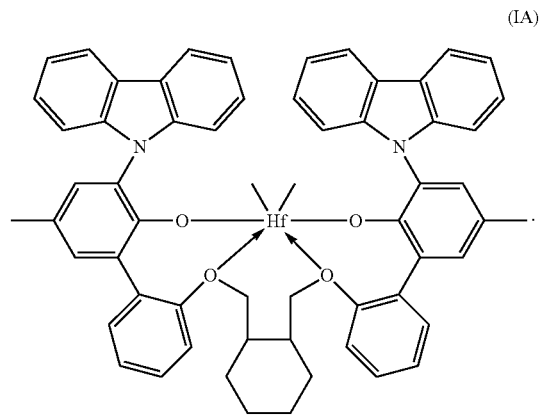

(IA)

The Ziegler/Natta catalysts suitable for use in the invention are typical supported, Ziegler-type catalysts, which are particularly useful at the high polymerization temperatures of the solution process. Examples of such compositions are those derived from organomagnesium compounds, alkyl halides or aluminum halides or hydrogen chloride, and a transition metal compound. Examples of such catalysts are described in U.S. Pat. Nos. 4,612,300; 4,314,912; and 4,547,475; the teachings of which are incorporated herein by reference.

Particularly suitable organomagnesium compounds include, for example, hydrocarbon soluble dihydrocarbylmagnesium, such as the magnesium dialkyls and the magnesium diaryls. Exemplary suitable magnesium dialkyls include, particularly, n-butyl-sec-butylmagnesium, diisopropylmagnesium, di-n-hexylmagnesium, isopropyl-n-butylmagnesium, ethyl-n-hexylmagnesium, ethyl-n-butylmagnesium, di-n-octylmagnesium, and others, wherein the alkyl has from 1 to 20 carbon atoms. Exemplary suitable magnesium diaryls include diphenylmagnesium, dibenzylmagnesium and ditolylmagnesium. Suitable organomagnesium compounds include alkyl and aryl magnesium alkoxides and aryloxides and aryl and alkyl magnesium halides, with the halogen-free organomagnesium compounds being more desirable.

Halide sources include active non-metallic halides, metallic halides, and hydrogen chloride. Suitable non-metallic halides are represented by the formula R'X, wherein R' is hydrogen or an active monovalent organic radical, and X is a halogen. Particularly suitable non-metallic halides include, for example, hydrogen halides and active organic halides, such as t-alkyl halides, allyl halides, benzyl halides and other active hydrocarbyl halides. By an active organic halide is meant a hydrocarbyl halide that contains a labile halogen at least as active, i.e., as easily lost to another compound, as the halogen of sec-butyl chloride, preferably as active as t-butyl chloride. In addition to the organic monohalides, it is understood that organic dihalides, trihalides and other polyhalides that are active, as defined hereinbefore, are also suitably employed. Examples of preferred active non-metallic halides, include hydrogen chloride, hydrogen bromide, t-butyl chloride, t-amyl bromide, allyl chloride, benzyl chloride, crotyl chloride, methylvinyl carbinyl chloride, a-phenylethyl bromide, diphenyl methyl chloride, and the like. Most preferred are hydrogen chloride, t-butyl chloride, allyl chloride and benzyl chloride.

Suitable metallic halides include those represented by the formula $MR_{y-a}X_a$, wherein: M is a metal of Groups IIB, IIIA or IVA of Mendeleev's periodic Table of Elements; R is a monovalent organic radical; X is a halogen; y has a value corresponding to the valence of M; and "a" has a value from 1 to y. Preferred metallic halides are aluminum halides of the formula $AlR_{3-a}X_a$, wherein each R is independently hydrocarbyl, such as alkyl; X is a halogen; and a is a number from 1 to 3. Most preferred are alkylaluminum halides, such as ethylaluminum sesquichloride, diethylaluminum chloride, ethylaluminum dichloride, and diethylaluminum bromide, with ethylaluminum dichloride being especially preferred. Alternatively, a metal halide, such as aluminum trichloride, or a combination of aluminum trichloride with an alkyl aluminum halide, or a trialkyl aluminum compound may be suitably employed.

Any of the conventional Ziegler-Natta transition metal compounds can be usefully employed, as the transition metal component in preparing the supported catalyst component. Typically, the transition metal component is a compound of a Group IVB, VB, or VIB metal. The transition metal component is generally, represented by the formulas: $TrX'_{4-q}(OR1)q$, $TrX'_{4-q}(R2)q$, $VOX'_3$ and $VO(OR)_3$.

Tr is a Group IVB, VB, or VIB metal, preferably a Group IVB or VB metal, preferably titanium, vanadium or zirconium; q is 0 or a number equal to, or less than, 4; X' is a halogen, and R1 is an alkyl group, aryl group or cycloalkyl group having from 1 to 20 carbon atoms; and R2 is an alkyl group, aryl group, aralkyl group, substituted aralkyls, and the like.

The aryl, aralkyls and substituted aralkys contain 1 to 20 carbon atoms, preferably 1 to 10 carbon atoms. When the transition metal compound contains a hydrocarbyl group, R2, being an alkyl, cycloalkyl, aryl, or aralkyl group, the hydrocarbyl group will preferably not contain an H atom in the position beta to the metal carbon bond. Illustrative, but non-limiting, examples of aralkyl groups are methyl, neopentyl, 2,2-dimethylbutyl, 2,2-dimethylhexyl; aryl groups such as benzyl; cycloalkyl groups such as 1-norbornyl. Mixtures of these transition metal compounds can be employed if desired.

Illustrative examples of the transition metal compounds include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_6H_{13})_2Cl_2$, $Ti(OC_8H_{17})_2Br_2$, and $Ti(OC_{12}H_{25})Cl_3$, $Ti(O\text{-}iC_3H_7)_4$, and $Ti(O\text{-}nC_4H_9)_4$. Illustrative examples of vanadium compounds include $VCl_4$, $VOCl_3$, $VO(OC_2H_5)_3$, and $VO(OC_4H_9)_3$. Illustrative examples of zirconium compounds include $ZrCl_4$, $ZrCl_3(OC_2H_5)$, $ZrCl_2(OC_2H_5)_2$, $ZrCl(OC_2H_5)_3$, $Zr(OC_2H_5)_4$, $ZrCl_3(OC_4H_9)$, $ZrCl_2(OC_4H_9)_2$, and $ZrCl(OC_4H_9)3$.

An inorganic oxide support may be used in the preparation of the catalyst, and the support may be any particulate oxide, or mixed oxide which has been thermally or chemically dehydrated, such that it is substantially free of adsorbed moisture. See U.S. Pat. Nos. 4,612,300; 4,314,912; and 4,547,475; the teachings of which are incorporated herein by reference.

In one embodiment, the composition comprises a MWCDI value greater than 0.9.

In one embodiment, the composition comprises a melt index ratio (I10/I2) that meets the following equation: $I10/I2 \geq 7.0 - 1.2 \times \log(I2)$.

The composition may comprise one embodiment, or a combination of two or more embodiments, as listed above for the "first composition."

An inventive process may comprise a combination of two or more embodiments described herein.

Co-Catalyst Component

The above described catalyst systems can be rendered catalytically active by contacting it to, or combining it with, the activating co-catalyst, or by using an activating technique, such as those known in the art, for use with metal-based olefin polymerization reactions. Suitable activating co-catalysts, for use herein, include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis. Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

Exemplary Lewis acid activating co-catalysts are Group 13 metal compounds containing from 1 to 3 hydrocarbyl substituents as described herein. In some embodiments, exemplary Group 13 metal compounds are tri(hydrocarbyl)-substituted-aluminum or tri(hydrocarbyl)-boron compounds. In some other embodiments, exemplary Group 13 metal compounds are tri(hydrocarbyl)-substituted-aluminum or tri(hydrocarbyl)-boron compounds are tri($(C_1\text{-}C_{10})$alkyl)aluminum or tri($(C_6\text{-}C_{18})$aryl)boron compounds and halogenated (including perhalogenated) derivatives thereof. In some other embodiments, exemplary Group 13 metal compounds are tris(fluoro-substituted phenyl)boranes, in other embodiments, tris(pentafluorophenyl)borane. In some embodiments, the activating co-catalyst is a tris($(C_1\text{-}C_{20})$ hydrocarbyl) borate (e.g., trityl tetrafluoroborate) or a tri (($C_1\text{-}C_{20}$)hydrocarbyl)ammonium tetra(($C_1\text{-}C_{20}$)hydrocarbyl)borane (e.g., bis(octadecyl)methylammonium tetrakis (pentafluorophenyl)borane). As used herein, the term "ammonium" means a nitrogen cation that is a (($C_1\text{-}C_{20}$) hydrocarbyl)$_4N^+$, a (($C_1\text{-}C_{20}$)hydrocarbyl)$_3N(H)^+$, a (($C_1$-$C_{20}$)hydrocarbyl)$_2N(H)_2^+$, ($C_1\text{-}C_{20}$)hydrocarbylN(H)$_3^+$, or $N(H)_4^+$, wherein each ($C_1\text{-}C_{20}$)hydrocarbyl may be the same or different.

Exemplary combinations of neutral Lewis acid activating co-catalysts include mixtures comprising a combination of a tri(($C_1\text{-}C_4$)alkyl)aluminum and a halogenated tri(($C_6\text{-}C_{18}$)

aryl)boron compound, especially a tris(pentafluorophenyl) borane. Other exemplary embodiments are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Exemplary embodiments ratios of numbers of moles of (metal-ligand complex): (tris(pentafluoro-phenylborane): (alumoxane) [e.g., (Group 4 metal-ligand complex):(tris(pentafluoro-phenylborane): (alumoxane)] are from 1:1:1 to 1:10:30, other exemplary embodiments are from 1:1:1.5 to 1:5:10.

Many activating co-catalysts and activating techniques have been previously taught, with respect to different metal-ligand complexes, in the following U.S. patents: U.S. Pat. Nos. 5,064,802; 5,153,157; 5,296,433; 5,321,106; 5,350, 723; 5,425,872; 5,625,087; 5,721,185; 5,783,512; 5,883, 204; 5,919,983; 6,696,379; and 7,163,907. Examples of suitable hydrocarbyloxides are disclosed in U.S. Pat. No. 5,296,433. Examples of suitable Bronsted acid salts for addition polymerization catalysts are disclosed in U.S. Pat. Nos. 5,064,802; 5,919,983; 5,783,512. Examples of suitable salts of a cationic oxidizing agent and a non-coordinating, compatible anion, as activating co-catalysts for addition polymerization catalysts, are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts, as activating co-catalysts for addition polymerization catalysts, are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B 1, beginning at column 50, at line 39, and going through column 56, at line 55, only the portion of which is incorporated by reference herein.

In some embodiments, the above described catalyst systems can be activated to form an active catalyst composition by combination with one or more cocatalyst, such as a cation forming cocatalyst, a strong Lewis acid, or a combination thereof. Suitable cocatalysts for use include polymeric or oligomeric aluminoxanes, especially methyl aluminoxane, as well as inert, compatible, noncoordinating, ion forming compounds. Exemplary suitable cocatalysts include, but are not limited to, modified methyl aluminoxane (MMAO), bis(hydrogenated tallow alkyl)methyl, tetrakis(pentafluorophenyl)borate(1-) amine, triethyl aluminum (TEA), and any combinations thereof.

In some embodiments, one or more of the foregoing activating co-catalysts are used in combination with each other. In one embodiment, a combination of a mixture of a tri(($C_1$-$C_4$)hydrocarbyl)aluminum, tri(($C_1$-$C_4$)hydrocarbyl)borane, or an ammonium borate with an oligomeric or polymeric alumoxane compound, can be used.

Additives, Additional Polymers and Applications

An inventive composition may comprise one or more additives. Additives include, but are not limited to, antistatic agents, color enhancers, dyes, lubricants, fillers (for example, $TiO_2$ or $CaCO_3$), opacifiers, nucleators, processing aids, pigments, primary anti-oxidants, secondary anti-oxidants, UV stabilizers, anti-blocks, slip agents, tackifiers, fire retardants, anti-microbial agents, odor reducer agents, anti-fungal agents, and combinations thereof. An inventive composition may comprise from about 0.001 to about 10 percent by the combined weight of such additives, based on the weight of the composition including such additives. In some embodiments, such as applications where fire resistance is important, the combined weight of such additives can be up to 40 weight percent.

An inventive composition may further comprise one or more other polymers. For example one or more other ethylene-based polymers (such polymers differ in one or more properties from the ethylene-based polymer of the first composition and the second ethylene-based polymer; i.e., density, melt index, comonomer, Mn, Mw, and/or MWD), or one or more propylene-based polymers, or combinations thereof. Such compositions may be blended via any method, known to a person of ordinary skill in the art, including, but not limited to, dry blending, and melt blending via any suitable equipment, for example, an extruder.

The invention provides for an article comprising at least one component formed from an inventive composition. Articles include, but are not limited to, artificial turf filaments, artificial turf, and similar structures.

Artificial Turf Filament

In some embodiments, the present invention relates to an artificial turf filament formed from any of the inventive compositions as described herein.

In embodiments herein, the artificial turf filaments may exhibit a shrink of less than 6.0%. All individual values and subranges of less than 6.0% are included and disclosed herein. For example, in some embodiments, the artificial turf filaments may exhibit a shrink lower than 5.8, 5.5%, 5.3%, 5.2%, 5.0%, or lower. The shrink may be determined by submerging 1 meter of yarn in a heated oil bath at 90° C. for 20 seconds.

In embodiments herein, the artificial turf filament may exhibit an elongation of at least 50%. The elongation is measured on a Zwick tensile tester on a filament length of 250 mm and extension rate of 250 mm/minute until the filament breaks. Elongation is the strain at break.

In embodiments herein, the artificial turf filaments may further include one or more additives. Nonlimiting examples of suitable additives include antioxidants, pigments, colorants, UV stabilizers, UV absorbers, curing agents, cross linking co-agents, boosters and retardants, processing aids, fillers, coupling agents, ultraviolet absorbers or stabilizers, antistatic agents, nucleating agents, slip agents, plasticizers, lubricants, viscosity control agents, tackifiers, anti-blocking agents, surfactants, extender oils, acid scavengers, and metal deactivators. Additives can be used in amounts ranging from less than about 0.01 wt % to more than about 10 wt % based on the weight of the composition.

The amount of the inventive composition to use in artificial turf filaments of the present invention can depend on a number of factors including, for example, the desired properties of the artificial turf filament, the desired properties of the artificial turf incorporating the filaments, the equipment available to manufacture the artificial turf filaments and/or the artificial turf, and others. An artificial turf filament of the present invention, in some embodiments, comprises at least 20 percent by weight of the inventive composition. In some embodiments, an artificial turf filament comprises 20 to 99 percent by weight of the inventive composition, or 20 to 94 percent by weight of the inventive composition, or 50 to 94 percent by weight of the inventive composition, or 80 to 94 percent by weight of the inventive composition, or 85 to 94 percent by weight of the inventive composition.

Artificial Turf Filament Process

The artificial turf filaments described herein may be made using any appropriate process for the production of artificial turf filament from polymer compositions as the artificial turf filaments described herein are process independent. Referring to FIG. 1, the following describes one such exemplary process 100 that may be used.

Artificial turf filaments may be made by extrusion. Suitable artificial turf filament extruders may be equipped with a single PE/PP general purpose screw and a melt pump ("gear pump" or "melt pump") to precisely control the consistency of polymer volume flow into the die 105. Artificial turf filament dies 105 may have multiple single holes for the individual filaments distributed over a circular or rectangular spinplate. The shape of the holes corresponds to the desired filament cross-section profile, including for example, rectangular, dog-bone, v-shaped, and Mexican hat. A standard spinplate has 50 to 160 die holes of specific dimensions. Lines can have output rates from 150 kg/h to 350 kg/h.

The artificial turf filaments 110 may be extruded into a water bath 115 with a die-to-water bath distance of from 16 to 40 mm Coated guiding bars in the water redirect the filaments 110 towards the first takeoff set of rollers 120. The linear speed of this first takeoff set of rollers 120 may vary from 15 to 70 m/min. The first takeoff set of rollers 120 can be heated and used to preheat the filaments 110 after the waterbath 115 and before entering the stretching oven 125. The stretching oven 125 may be a heated air or water bath oven. The filaments 110 may be stretched in the stretching oven 125 to a predetermined stretched ratio. In some embodiments, the stretch ratio is at least 4. In other embodiments, the stretch ratio is at least 4.5, 4.8, 5.0, 5.2, or 5.5. The stretching ratio is the ratio between the speed of the second takeoff set of rollers 130 after the stretching oven and the speed of the first takeoff set of rollers 120 before the stretching oven (V2/V1 as shown in FIG. 1). The second takeoff set of rollers 120 may be run at a different (higher or lower) speed than the first set of rollers 130.

After the filaments 110 are passed over the second takeoff set of rollers 130, they are then drawn through a set of three annealing ovens 135, 140, and 145. The three annealing ovens 135, 140, and 145 may be either a hot air oven with co- or countercurrent hot air flow, which can be operated from 50 to 150° C. or a hot water-oven, wherein the filaments 110 are oriented at temperatures from 50 to 98° C. At the exit of the first annealing oven 135, the filaments 110 are passed onto a third set of rollers 150 that may be run at a different (higher or lower) speed than the second set of rollers 130. The linear velocity ratio of the third set of rollers 150 located after the oven to the second set of rollers 130 located in front of the oven may be referred to as either a stretching or relaxation ratio. At the exit of the second annealing oven 140, the filaments 110 are passed onto a fourth set of rollers 155 that may be run at a different (higher or lower) speed than the third set of rollers 150. At the exit of the third annealing oven 145, the filaments 110 are passed onto a fifth set of rollers 160 that may be run at a different (higher or lower) speed than the fourth set of rollers 155.

In some embodiments, a method of manufacturing an artificial turf filament comprises providing any of the inventive compositions previously described herein, and extruding the inventive composition into an artificial turf filament. The artificial turf filament may be extruded to a specified width, thickness, and/or cross-sectional shape depending on the physical dimensions of the extruder. As mentioned above, the artificial turf filament can include a monofilament, a multifilament, a film, a fiber, a yarn, such as, for example, tape yarn, fibrillated tape yarn, or slit-film yarn, a continuous ribbon, and/or other fibrous materials used to form synthetic grass blades or strands of an artificial turf field.

The artificial turf filament may optionally undergo further post-extrusion processing (e.g., annealing, cutting, etc.).

Artificial Turf

Figure 2:
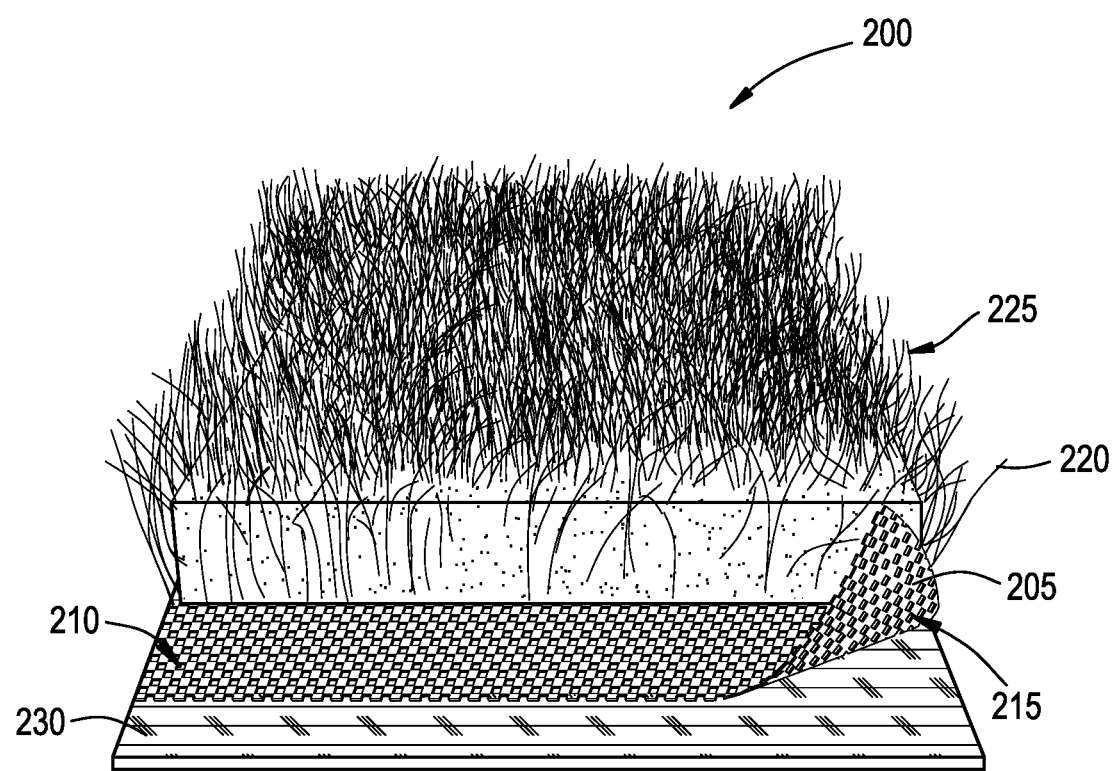
FIG. 2 pictorially depicts a cutaway view of an artificial turf according to one or more embodiments shown and described herein.

One or more embodiments of the artificial turf filaments described herein may be used to form an artificial turf field. Referring to FIG. 2, depicted is a cutaway view of an artificial turf field 200 according to one or more embodiments shown and/or described herein. The artificial turf field 200 comprises a primary backing 205 having a top side 210 and a bottom side 215; and at least one artificial turf filament 220 as previously described herein. The at least one artificial turf filament 220 is affixed to the primary backing 205 such that the at least one artificial turf filament 220 provides a tufted face 225 extending outwardly from the top side 210 of the primary backing 205. As used herein, "affix," "affixed," or "affixing" includes, but is not limited to, coupling, attaching, connecting, fastening, joining, linking or securing one object to another object through a direct or indirect relationship. The tufted face 225 extends from the top side 210 of the primary backing 205, and can have a cut pile design, where the artificial turf filament loops may be cut, either during tufting or after, to produce a pile of single artificial turf filament ends instead of loops.

The primary backing 205 can include, but is not limited to, woven, knitted, or non-woven fibrous webs or fabrics made of one or more natural or synthetic fibers or yarns, such as polypropylene, polyethylene, polyamides, polyesters, and rayon. The artificial turf field 200 may further comprise a secondary backing 230 bonded to at least a portion of the bottom side 215 of the primary backing 205 such that the at least one artificial turf filament 220 is affixed in place to the bottom side 215 of the primary backing 205. The secondary backing 230 may comprise polyurethane (including, for example, polyurethane supplied under the name ENFORCER™ or ENHANCER™ available from The Dow Chemical Company) or latex-based materials, such as, styrene-butadiene latex, or acrylates.

The primary backing 205 and/or secondary backing 230 may have apertures through which moisture can pass. The apertures may be generally annular in configuration and are spread throughout the primary backing 205 and/or secondary backing 230. Of course, it should be understood that there may be any number of apertures, and the size, shape and location of the apertures may vary depending on the desired features of the artificial turf field 200.

The artificial turf field 200 may be manufactured by providing at least one artificial turf filament 220 as described herein and affixing the at least one artificial turf filament 220 to a primary backing 205 such that that at least one artificial turf filament 220 provides a tufted face 225 extending outwardly from a top side 210 of the primary backing 205. The artificial turf field 200 may further be manufactured by bonding a secondary backing 230 to at least a portion of the bottom side 215 of the primary backing 205 such that the at least one artificial turf filament 220 is affixed in place to the bottom side 215 of the primary backing 205.

The artificial turf field 200 may optionally comprise a shock absorption layer underneath the secondary backing of the artificial turf field. The shock absorption layer can be made from polyurethane, PVC foam plastic or polyurethane foam plastic, a rubber, a closed-cell crosslinked polyethylene foam, a polyurethane underpad having voids, elastomer foams of polyvinyl chloride, polyethylene, polyurethane, and polypropylene. Non-limiting examples of a shock absorption layer are DOW® ENFORCER™ Sport Polyurethane Systems, and DOW® ENHANCER™ Sport Polyurethane Systems.

The artificial turf field 200 may optionally comprise an infill material. Suitable infill materials include, but are not limited to, mixtures of granulated rubber particles like SBR (styrene butadiene rubber) recycled from car tires, EPDM (ethylene-propylene-diene monomer), other vulcanised rubbers or rubber recycled from belts, thermoplastic elastomers (TPEs) and thermoplastic vulcanizates (TPVs).

The artificial turf field 200 may optionally comprise a drainage system. The drainage system allows water to be removed from the artificial turf field and prevents the field from becoming saturated with water. Nonlimiting examples of drainage systems include stone-based drainage systems, EXCELDRAIN™ Sheet 100, EXCELDRAIN™ Sheet 200, AND EXCELDRAIN™ EX-T STRIP (available from American Wick Drain Corp., Monroe, N.C.).

Definitions

Unless stated to the contrary, implicit from the context, or customary in the art, all parts and percents are based on weight, and all test methods are current as of the filing date of this disclosure.

The term "composition," as used herein, includes material(s) which comprise the composition, as well as reaction products and decomposition products formed from the materials of the composition.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities may be incorporated into and/or within the polymer.

The term "interpolymer," as used herein, refers to a polymer prepared by the polymerization of at least two different types of monomers. The generic term interpolymer thus includes copolymers (employed to refer to polymers prepared from two different types of monomers), and polymers prepared from more than two different types of monomers.

The term, "olefin-based polymer," as used herein, refers to a polymer that comprises, in polymerized form, a majority amount of olefin monomer, for example ethylene or propylene (based on the weight of the polymer), and optionally may comprise at least one polymerized comonomer.

The term, "ethylene-based polymer," as used herein, refers to a polymer that comprises a majority amount of polymerized ethylene monomer (based on the total weight of the polymer), and optionally may comprise at least one polymerized comonomer.

The term, "ethylene/α-olefin interpolymer," as used herein, refers to an interpolymer that comprises, in polymerized form, a majority amount of ethylene monomer (based on the weight of the interpolymer), and at least one α-olefin.

The term, "ethylene/α-olefin copolymer," as used herein, refers to a copolymer that comprises, in polymerized form, a majority amount of ethylene monomer (based on the weight of the copolymer), and an α-olefin, as the only two monomer types.

The term "propylene-based polymer," as used herein, refers to a polymer that comprises, in polymerized form, a majority amount of propylene monomer (based on the total weight of the polymer) and optionally may comprise at least one polymerized comonomer.

The term "filament" refers to monofilaments, multifilaments, extruded films, fibers, yarns, such as, for example, tape yarns, fibrillated tape yarn, slit-film yarn, continuous ribbon, and/or other fibrous materials used to form synthetic grass blades or strands of an artificial turf field.

Test Methods

Melt Index

Melt indices $I_2$ (or I2) and $I_{10}$ (or I10) were measured in accordance to ASTM D-1238 (method B) at 190° C. and at 2.16 kg and 10 kg load, respectively. Their values are reported in g/10 min.

Density

Samples for density measurement were prepared according to ASTM D4703. Measurements were made, according to ASTM D792, Method B, within one hour of sample pressing.

Dynamic Shear Rheology

Each sample was compression-molded into "3 mm thick× 25 mm diameter" circular plaque, at 177° C., for five minutes, under 10 MPa pressure, in air. The sample was then taken out of the press and placed on a counter top to cool.

Constant temperature, frequency sweep measurements were performed on an ARES strain controlled rheometer (TA Instruments), equipped with 25 mm parallel plates, under a nitrogen purge. For each measurement, the rheometer was thermally equilibrated, for at least 30 minutes, prior to zeroing the gap. The sample disk was placed on the plate, and allowed to melt for five minutes at 190° C. The plates were then closed to 2 mm, the sample trimmed, and then the test was started. The method had an additional five minute delay built in, to allow for temperature equilibrium. The experiments were performed at 190° C., over a frequency range from 0.1 to 100 rad/s, at five points per decade interval. The strain amplitude was constant at 10%. The stress response was analyzed in terms of amplitude and phase, from which the storage modulus (G'), loss modulus (G"), complex modulus (G*), dynamic viscosity (η or Eta*), and tan δ (or tan delta) were calculated.

Conventional Gel Permeation Chromatography (Cony. GPC)

A GPC-IR high temperature chromatographic system from PolymerChar (Valencia, Spain), was equipped with a Precision Detectors (Amherst, Mass.), 2-angle laser light scattering detector Model 2040, an IR5 infra-red detector and a 4-capillary viscometer, both from PolymerChar. Data collection was performed using PolymerChar Instrument Control software and data collection interface. The system was equipped with an on-line, solvent degas device and pumping system from Agilent Technologies (Santa Clara, Calif.).

Injection temperature was controlled at 150 degrees Celsius. The columns used, were three, 10-micron "Mixed-B" columns from Polymer Laboratories (Shropshire, UK). The solvent used was 1,2,4-trichlorobenzene. The samples were prepared at a concentration of "0.1 grams of polymer in 50 milliliters of solvent." The chromatographic solvent and the sample preparation solvent each contained "200 ppm of butylated hydroxytoluene (BHT)." Both solvent sources were nitrogen sparged. Ethylene-based polymer samples were stirred gently at 160 degrees Celsius for three hours. The injection volume was "200 microliters,' and the flow rate was "1 milliliters/minute." The GPC column set was calibrated by running 21 "narrow molecular weight distribution" polystyrene standards. The molecular weight (MW) of the standards ranges from 580 to 8,400,000 g/mole, and the standards were contained in six "cocktail" mixtures. Each standard mixture had at least a decade of separation between individual molecular weights. The standard mixtures were purchased from Polymer Laboratories. The polystyrene standards were prepared at "0.025 g in 50 mL of solvent" for molecular weights equal to, or greater than, 1,000,000 g/mole, and at "0.050 g in 50 mL of solvent" for molecular weights less than 1,000,000 g/mole.

The polystyrene standards were dissolved at 80° C., with gentle agitation, for 30 minutes. The narrow standards mixtures were run first, and in order of decreasing "highest molecular weight component," to minimize degradation. The polystyrene standard peak molecular weights were converted to polyethylene molecular weight using Equation 1 (as described in Williams and Ward, *J. Polym. Sci.*, Polym. Letters, 6, 621 (1968)):

$$M \text{polyethylene} = A \times (M \text{polystyrene})^B \quad \text{(Eqn. 1)},$$

where M is the molecular weight, A is equal to 0.4316 and B is equal to 1.0.

Number-average molecular weight (Mn(conv gpc)), weight average molecular weight (Mw-conv gpc), and z-average molecular weight (Mz(conv gpc)) were calculated according to Equations 2-4 below.

$$Mn(conv\ gpc) = \frac{\sum_{i=RV_{integration\ start}}^{i=RV_{integration\ end}} (IR_{measurement\ channel_i})}{\sum_{i=RV_{integration\ start}}^{i=RV_{integration\ end}} \left(\frac{IR_{measurement\ channel_i}}{M_{PE_i}}\right)} \quad \text{(Eqn. 2)}$$

$$Mw(conv\ gpc) = \frac{\sum_{i=RV_{integration\ start}}^{i=RV_{integration\ end}} (M_{PE_i} IR_{measurement\ channel_i})}{\sum_{i=RV_{integration\ start}}^{i=RV_{integration\ end}} (IR_{measurement\ channel_i})} \quad \text{(Eqn. 3)}$$

$$Mz(conv\ gpc) = \frac{\sum_{i=RV_{integration\ start}}^{i=RV_{integration\ end}} (M_{PE_i}^2 IR_{measurement\ channel_i})}{\sum_{i=RV_{integration\ start}}^{i=RV_{integration\ end}} (M_{PE_i} IR_{measurement\ channel_i})} \quad \text{(Eqn. 4)}$$

In Equations 2-4, the RV is column retention volume (linearly-spaced), collected at "1 point per second," the IR is the baseline-subtracted IR detector signal, in Volts, from the IR5 measurement channel of the GPC instrument, and $M_{PE}$ is the polyethylene-equivalent MW determined from Equation 1. Data calculation were performed using "GPC One software (version 2.013H)" from PolymerChar.

Creep Zero Shear Viscosity Measurement Method

Zero-shear viscosities were obtained via creep tests, which were conducted on an AR-G2 stress controlled rheometer (TA Instruments; New Castle, Del.), using "25-mm-diameter" parallel plates, at 190° C. The rheometer oven was set to test temperature for at least 30 minutes, prior to zeroing the fixtures. At the testing temperature, a compression molded sample disk was inserted between the plates, and allowed to come to equilibrium for five minutes. The upper plate was then lowered down to 50 µm (instrument setting) above the desired testing gap (1.5 mm). Any superfluous material was trimmed off, and the upper plate was lowered to the desired gap. Measurements were done under nitrogen purging, at a flow rate of 5 L/min. The default creep time was set for two hours. Each sample was compression-molded into a "2 mm thick×25 mm diameter" circular plaque, at 177° C., for five minutes, under 10 MPa pressure, in air. The sample was then taken out of the press and placed on a counter top to cool. A constant low shear stress of 20 Pa was applied for all of the samples, to ensure that the steady state shear rate was low enough to be in the Newtonian region. The resulting steady state shear rates were in the range from $10^{-3}$ to $10^{-4}$ s$^{-1}$ for the samples in this study. Steady state was determined by taking a linear regression for all the data, in the last 10% time window of the plot of "log (J(t)) vs. log(t)," where J(t) was creep compliance and t was creep time. If the slope of the linear regression was greater than 0.97, steady state was considered to be reached, then the creep test was stopped. In all cases in this study, the slope meets the criterion within one hour. The steady state shear rate was determined from the slope of the linear regression of all of the data points, in the last 10% time window of the plot of "ε vs. t," where ε was strain. The zero-shear viscosity was determined from the ratio of the applied stress to the steady state shear rate.

In order to determine if the sample was degraded during the creep test, a small amplitude oscillatory shear test was conducted before, and after, the creep test, on the same specimen from 0.1 to 100 rad/s. The complex viscosity values of the two tests were compared. If the difference of the viscosity values, at 0.1 rad/s, was greater than 5%, the sample was considered to have degraded during the creep test, and the result was discarded.

Zero-Shear Viscosity Ratio (ZSVR) is defined as the ratio of the zero-shear viscosity (ZSV) of the branched polyethylene material to the ZSV of a linear polyethylene material (see ANTEC proceeding below) at the equivalent weight average molecular weight (Mw(conv gpc)), according to the following Equation 5:

$$ZSVR = \frac{\eta_{0B}}{\eta_{0L}} = \frac{\eta_{0B}}{2.29^{-15} M_{w(conv \cdot gpc)}^{3.65}}. \quad \text{(Eqn. 5)}$$

The ZSV value was obtained from creep test, at 190° C., via the method described above. The Mw(conv gpc) value was determined by the conventional GPC method (Equation 3), as discussed above. The correlation between ZSV of linear polyethylene and its Mw(conv gpc) was established based on a series of linear polyethylene reference materials. A description for the ZSV-Mw relationship can be found in the ANTEC proceeding: Karjala et al., *Detection of Low Levels of Long-chain Branching in Polyolefins*, Annual Technical Conference—Society of Plastics Engineers (2008), 66th 887-891.

$^1$H NMR Method

A stock solution (3.26 g) was added to "0.133 g of the polymer sample" in 10 mm NMR tube. The stock solution was a mixture of tetrachloroethane-d$_2$ (TCE) and perchloroethylene (50:50, w:w) with 0.001M Cr$^{3+}$. The solution in the tube was purged with $N_2$, for 5 minutes, to reduce the amount of oxygen. The capped sample tube was left at room temperature, overnight, to swell the polymer sample. The sample was dissolved at 110° C. with periodic vortex mixing. The samples were free of the additives that may contribute to unsaturation, for example, slip agents such as erucamide. Each $^1$H NMR analysis was run with a 10 mm cryoprobe, at 120° C., on Bruker AVANCE 400 MHz spectrometer.

Two experiments were run to get the unsaturation: the control and the double presaturation experiments. For the control experiment, the data was processed with an exponential window function with LB=1 Hz, and the baseline was corrected from 7 to −2 ppm. The signal from residual $^1$H of TCE was set to 100, and the integral $I_{total}$ from −0.5 to 3 ppm was used as the signal from whole polymer in the control experiment. The "number of $CH_2$ group, $NCH_2$," in the polymer was calculated as follows in Equation 1A:

$$NCH_2 = I_{total}/2 \quad \text{(Eqn. 1A)}.$$

For the double presaturation experiment, the data was processed with an exponential window function with LB=1 Hz, and the baseline was corrected from about 6.6 to 4.5 ppm. The signal from residual $^1$H of TCE was set to 100, and the corresponding integrals for unsaturations ($I_{vinylene}$, $I_{trisubstituted}$, $I_{vinyl}$ and $I_{vinylidene}$) were integrated. It is well known to use NMR spectroscopic methods for determining polyethylene unsaturation, for example, see Busico, V., et al., *Macromolecules*, 2005, 38, 6988. The number of unsaturation unit for vinylene, trisubstituted, vinyl and vinylidene were calculated as follows:

$$N_{vinylene} = I_{vinylene}/2 \quad \text{(Eqn. 2A)},$$

$$N_{trisubstituted} = I_{trisubstitute} \quad \text{(Eqn. 3A)},$$

$$N_{vinyl} = I_{vinyl}/2 \quad \text{(Eqn. 4A)},$$

$$N_{vinylidene} = I_{vinylidene}/2 \quad \text{(Eqn. 5A)}.$$

The unsaturation units per 1,000 carbons, all polymer carbons including backbone carbons and branch carbons, were calculated as follows:

$$N_{vinylene}/1,000 \, C = (N_{vinylene}/NCH_2)*1,000 \quad \text{(Eqn. 6A)},$$

$$N_{trisubstituted}/1,000 \, C = (N_{trisubstituted}/NCH_2)*1,000 \quad \text{(Eqn. 7A)},$$

$$N_{vinyl}/1,000 \, C = (N_{vinyl}/NCH_2)*1,000 \quad \text{(Eqn. 8A)},$$

$$N_{vinylidene}/1,000 \, C = (N_{vinylidene}/NCH_2)*1,000 \quad \text{(Eqn. 9A)},$$

The chemical shift reference was set at 6.0 ppm for the $^1$H signal from residual proton from TCE-d2. The control was run with ZG pulse, NS=4, DS=12, SWH=10,000 Hz, AQ=1.64 s, D1=14 s. The double presaturation experiment was run with a modified pulse sequence, with O1P=1.354 ppm, O2P=0.960 ppm, PL9=57 db, PL21=70 db, NS=100, DS=4, SWH=10,000 Hz, AQ=1.64 s, D1=1 s (where D1 is the presaturation time), D13=13 s. Only the vinyl levels were reported in Table 2 below.

$^{13}$C NMR Method

Samples are prepared by adding approximately 3 g of a 50/50 mixture of tetra-chloroethane-d2/orthodichlorobenzene, containing 0.025 M $Cr(AcAc)_3$, to a "0.25 g polymer sample" in a 10 mm NMR tube. Oxygen is removed from the sample by purging the tube headspace with nitrogen. The samples are then dissolved, and homogenized, by heating the tube and its contents to 150° C., using a heating block and heat gun. Each dissolved sample is visually inspected to ensure homogeneity.

All data are collected using a Bruker 400 MHz spectrometer. The data is acquired using a 6 second pulse repetition delay, 90-degree flip angles, and inverse gated decoupling with a sample temperature of 120° C. All measurements are made on non-spinning samples in locked mode. Samples are allowed to thermally equilibrate for 7 minutes prior to data acquisition. The 13C NMR chemical shifts were internally referenced to the EEE triad at 30.0 ppm.

C13 NMR Comonomer Content: It is well known to use NMR spectroscopic methods for determining polymer composition. ASTM D 5017-96; J. C. Randall et al., in "NMR and Macromolecules" ACS Symposium series 247; J. C. Randall, Ed., Am. Chem. Soc., Washington, D.C., 1984, Ch. 9; and J. C. Randall in "Polymer Sequence Determination", Academic Press, New York (1977) provide general methods of polymer analysis by NMR spectroscopy.

Molecular Weighted Comonomer Distribution Index (MWCDI)

A GPC-IR, high temperature chromatographic system from PolymerChar (Valencia, Spain) was equipped with a Precision Detectors' (Amherst, Mass.) 2-angle laser light scattering detector Model 2040, and an IR5 infra-red detector (GPC-IR) and a 4-capillary viscometer, both from PolymerChar. The "15-degree angle" of the light scattering detector was used for calculation purposes. Data collection was performed using PolymerChar Instrument Control software and data collection interface. The system was equipped with an on-line, solvent degas device and pumping system from Agilent Technologies (Santa Clara, Calif.).

Injection temperature was controlled at 150 degrees Celsius. The columns used, were four, 20-micron "Mixed-A" light scattering columns from Polymer Laboratories (Shropshire, UK). The solvent was 1,2,4-trichlorobenzene. The samples were prepared at a concentration of "0.1 grams of polymer in 50 milliliters of solvent." The chromatographic solvent and the sample preparation solvent each contained "200 ppm of butylated hydroxytoluene (BHT)." Both solvent sources were nitrogen sparged. Ethylene-based polymer samples were stirred gently, at 160 degrees Celsius, for three hours. The injection volume was "200 microliters," and the flow rate was "1 milliliters/minute."

Calibration of the GPC column set was performed with 21 "narrow molecular weight distribution" polystyrene standards, with molecular weights ranging from 580 to 8,400,000 g/mole. These standards were arranged in six "cocktail" mixtures, with at least a decade of separation between individual molecular weights. The standards were purchased from Polymer Laboratories (Shropshire UK). The polystyrene standards were prepared at "0.025 grams in 50 milliliters of solvent" for molecular weights equal to, or greater than, 1,000,000 g/mole, and at "0.050 grams in 50 milliliters of solvent" for molecular weights less than 1,000,000 g/mole. The polystyrene standards were dissolved at 80 degrees Celsius, with gentle agitation, for 30 minutes. The narrow standards mixtures were run first, and in order of decreasing "highest molecular weight component," to minimize degradation. The polystyrene standard peak molecular weights were converted to polyethylene molecular weights using Equation 1B (as described in Williams and Ward, J. Polym. Sci., Polym. Let., 6, 621 (1968)):

$$M\text{polyethylene} = A \times (M\text{polystyrene})^B \quad \text{(Eqn. 1B)},$$

where M is the molecular weight, A has a value of approximately 0.40 and B is equal to 1.0. The A value was adjusted between 0.385 and 0.425 (depending upon specific column-set efficiency), such that NBS 1475A (NIST) linear polyethylene weight-average molecular weight corresponded to 52,000 g/mole, as calculated by Equation 3B, below:

$$Mn(LALS\ gpc) = \frac{\sum_{i=RV_{integration\ start}}^{i=RV_{integration\ end}} (IR_{measurement\ channel_i})}{\sum_{i=RV_{integration\ start}}^{i=RV_{integration\ end}} \left(\frac{IR_{measurement\ channel_i}}{M_{PE_i}}\right)} \quad \text{(Eqn. 2B)}$$

$$Mw(LALS\ gpc) = \frac{\sum_{i=RV_{integration\ start}}^{i=RV_{integration\ end}} (M_{PE_i} IR_{measurement\ channel_i})}{\sum_{i=RV_{integration\ start}}^{i=RV_{integration\ end}} (IR_{measurement\ channel_i})} \quad \text{(Eqn. 3B)}$$

In Equations 2B and 3B, RV is column retention volume (linearly-spaced), collected at "1 point per second." The IR is the baseline-subtracted IR detector signal, in Volts, from the measurement channel of the GPC instrument, and the $M_{PE}$ is the polyethylene-equivalent MW determined from Equation 1B. Data calculation were performed using "GPC One software (version 2.013H)" from PolymerChar.

A calibration for the IR5 detector ratios was performed using at least ten ethylene-based polymer standards (polyethylene homopolymer and ethylene/octene copolymers; narrow molecular weight distribution and homogeneous comonomer distribution) of known short chain branching (SCB) frequency (measured by the $^{13}C$ NMR Method, as discussed above), ranging from homopolymer (0 SCB/1000 total C) to approximately 50 SCB/1000 total C, where total C=carbons in backbone+carbons in branches. Each standard had a weight-average molecular weight from 36,000 g/mole to 126,000 g/mole, as determined by the GPC-LALS processing method described above. Each standard had a molecular weight distribution (Mw/Mn) from 2.0 to 2.5, as determined by the GPC-LALS processing method described above. Polymer properties for the SCB standards are shown in Table A.

TABLE A

"SCB" Standards

| Wt % Comonomer | IR5 Area ratio | SCB/1000 Total C | Mw | Mw/Mn |
|---|---|---|---|---|
| 23.1 | 0.2411 | 28.9 | 37,300 | 2.22 |
| 14.0 | 0.2152 | 17.5 | 36,000 | 2.19 |
| 0.0 | 0.1809 | 0.0 | 38,400 | 2.20 |
| 35.9 | 0.2708 | 44.9 | 42,200 | 2.18 |
| 5.4 | 0.1959 | 6.8 | 37,400 | 2.16 |
| 8.6 | 0.2043 | 10.8 | 36,800 | 2.20 |
| 39.2 | 0.2770 | 49.0 | 125,600 | 2.22 |
| 1.1 | 0.1810 | 1.4 | 107,000 | 2.09 |
| 14.3 | 0.2161 | 17.9 | 103,600 | 2.20 |
| 9.4 | 0.2031 | 11.8 | 103,200 | 2.26 |

The "IR5 Area Ratio (or "IR5$_{Methyl\ Channel\ Area}$/IR5$_{Measurement\ Channel\ Area}$")" of "the baseline-subtracted area response of the IR5 methyl channel sensor" to "the baseline-subtracted area response of IR5 measurement channel sensor" (standard filters and filter wheel as supplied by PolymerChar: Part Number IR5_FWM01 included as part of the GPC-IR instrument) was calculated for each of the "SCB" standards. A linear fit of the SCB frequency versus the "IR5 Area Ratio" was constructed in the form of the following Equation 4B:

$$\text{SCB/1000 total } C = A_0 + [A_1 \times (\text{IR5}_{Methyl\ Channel\ Area}/\text{IR5}_{Measurement\ Channel\ Area})] \quad \text{(Eqn. 4B)},$$

where $A_0$ is the "SCB/1000 total C" intercept at an "IR5 Area Ratio" of zero, and $A_1$ is the slope of the "SCB/1000 total C" versus "IR5 Area Ratio," and represents the increase in the "SCB/1000 total C" as a function of "IR5 Area Ratio."

A series of "linear baseline-subtracted chromatographic heights" for the chromatogram generated by the "IR5 methyl channel sensor" was established as a function of column elution volume, to generate a baseline-corrected chromatogram (methyl channel). A series of "linear baseline-subtracted chromatographic heights" for the chromatogram generated by the "IR5 measurement channel" was established as a function of column elution volume, to generate a base-line-corrected chromatogram (measurement channel).

The "IR5 Height Ratio" of "the baseline-corrected chromatogram (methyl channel)" to "the baseline-corrected chromatogram (measurement channel)" was calculated at each column elution volume index (each equally-spaced index, representing 1 data point per second at 1 ml/min elution) across the sample integration bounds. The "IR5 Height Ratio" was multiplied by the coefficient $A_1$, and the coefficient $A_0$ was added to this result, to produce the predicted SCB frequency of the sample. The result was converted into mole percent comonomer, as follows in Equation 5B:

$$\text{Mole Percent Comonomer} = \{SCB_f/[SCB_f + ((1000 - SCB_f * \text{Length of comonomer})/2)]\} * 100 \quad \text{(Eqn. 5B)},$$

where "$SCB_f$" is the "SCB per 1000 total C", and the "Length of comonomer"=8 for octene, 6 for hexene, and so forth.

Each elution volume index was converted to a molecular weight value ($Mw_i$) using the method of Williams and Ward (described above; Eqn. 1B). The "Mole Percent Comonomer (y axis)" was plotted as a function of $Log(Mw_i)$, and the slope was calculated between $Mw_i$ of 15,000 and $Mw_i$ of 150,000 g/mole (end group corrections on chain ends were omitted for this calculation). An EXCEL linear regression was used to calculate the slope between, and including, $Mw_i$ from 15,000 to 150,000 g/mole. This slope is defined as the molecular weighted comonomer distribution index (MWCDI=Molecular Weighted Comonomer Distribution Index).

Representative Determination of MWCDI (Inventive First Composition 2)

Figure 3:
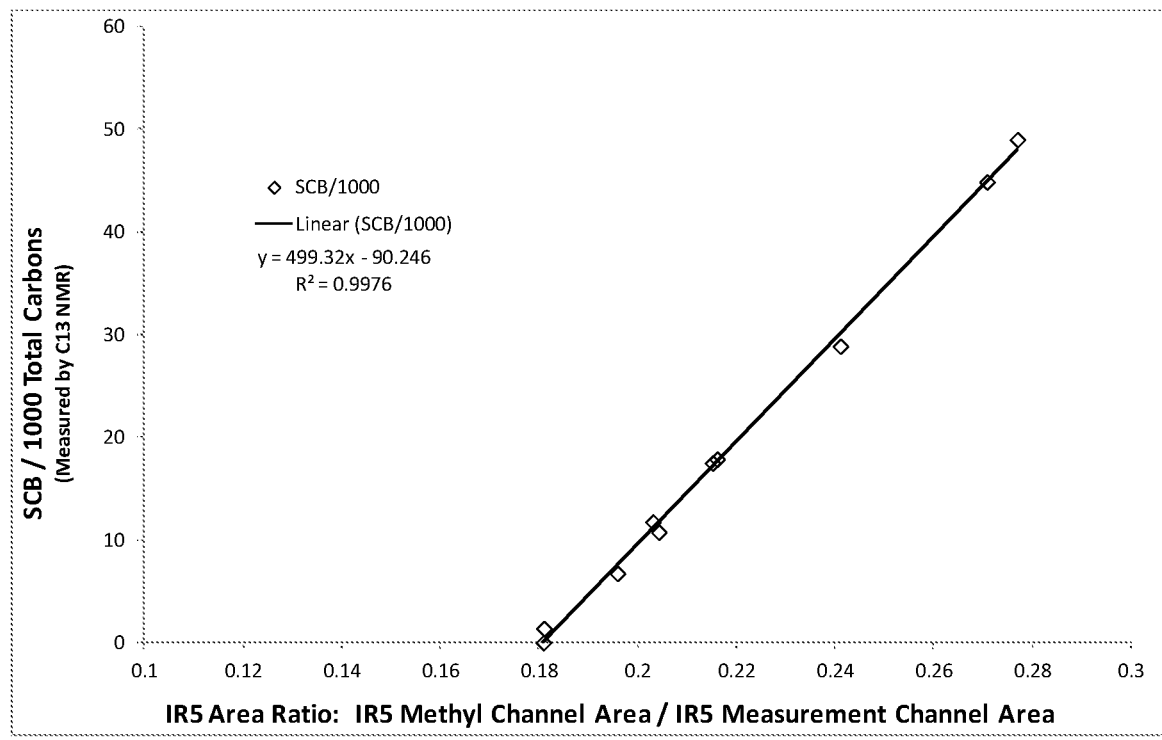
FIG. 3 depicts the plot of "$SCB_f$ versus IR5 Area Ratio" for ten SCB Standards.

A plot of the measured "SCB per 1000 total C (=$SCB_f$)" versus the observed "IR5 Area Ratio" of the SCB standards was generated (see FIG. 3), and the intercept ($A_0$) and slope ($A_1$) were determined Here, $A_0$=−90.246 SCB/1000 total C; and $A_1$=499.32 SCB/1000 total C.

Figure 4:
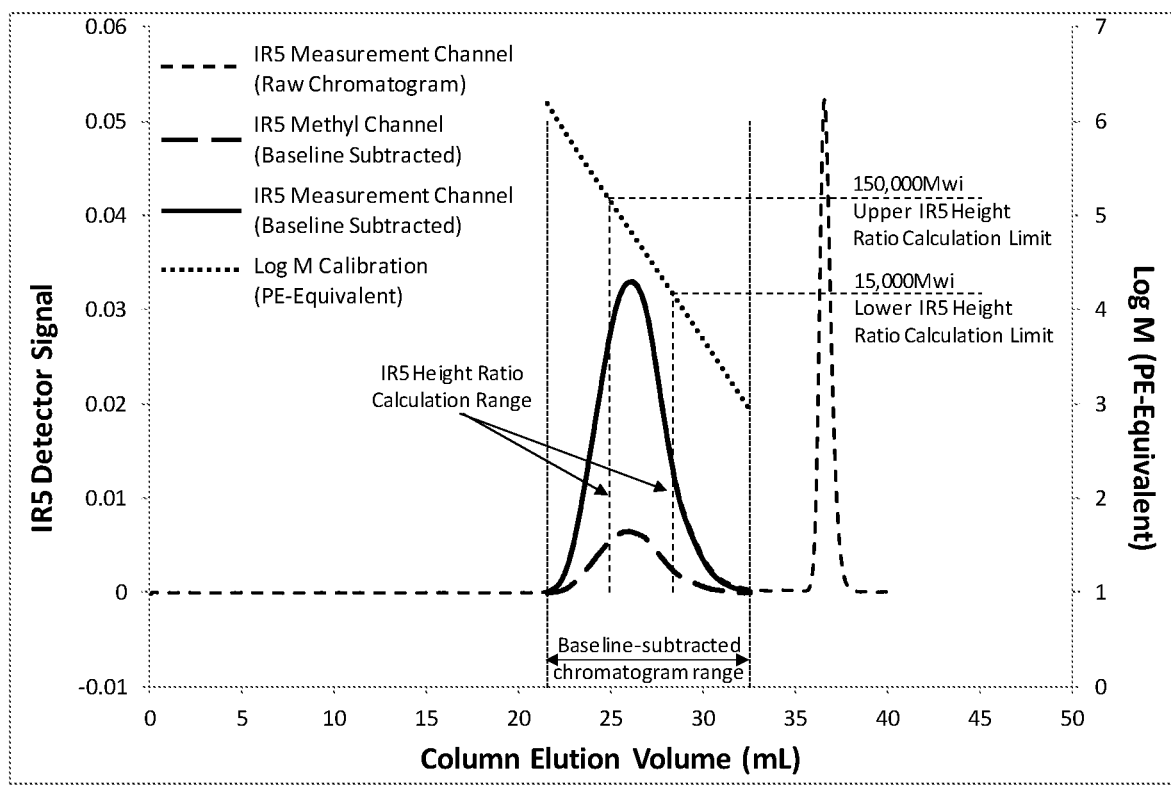
FIG. 4 depicts the several GPC profiles for the determination of IR5 Height Ratio for Inventive First Composition 2.
Figure 5:
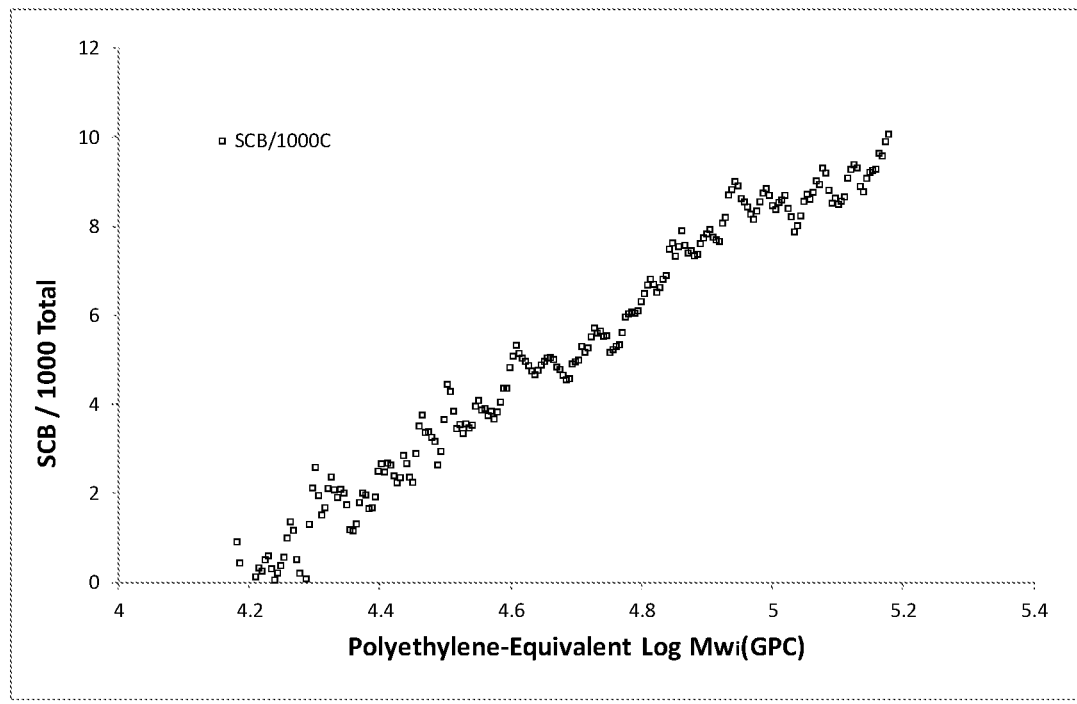
FIG. 5 depicts the plot of "$SCB_f$ versus Polyethylene Equivalent molecular Log $Mw_i$ (GPC)" for Inventive First Composition 2.

The "IR5 Height Ratio" was determined for Inventive Example 2 (see integration shown in FIG. 4). This height ratio (IR5 Height Ratio of Inventive Example 2) was multiplied by the coefficient $A_1$, and the coefficient $A_0$ was added to this result, to produce the predicted SCB frequency of this example, at each elution volume index, as described above ($A_0$=−90.246 SCB/1000 total C; and $A_1$=499.32 SCB/1000 total C). The $SCB_f$ was plotted as a function of polyethylene-equivalent molecular weight, as determined using Equation 1B, as discussed above. See FIG. 5 (Log Mwi used as the x-axis).

Figure 6:
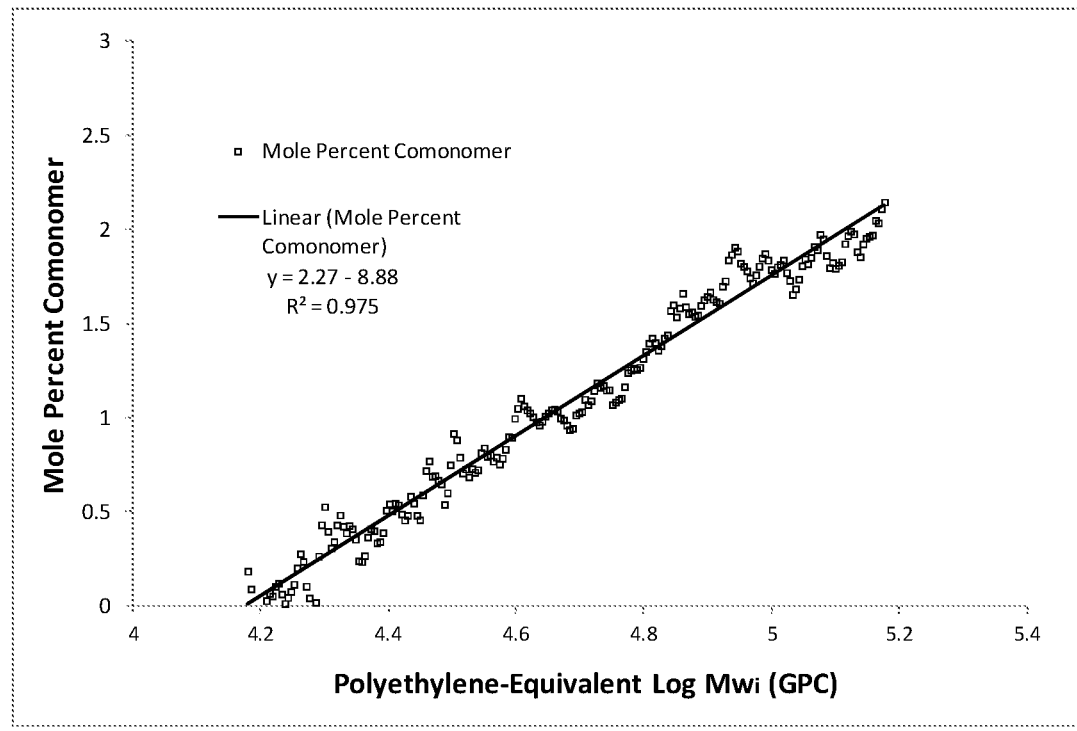
FIG. 6 depicts a plot of the "Mole Percent Comonomer versus Polyethylene Equivalent $Log_{Mwi}$ (GPC)" for Inventive First Composition 2.

The SCB$_f$ was converted into "Mole Percent Comonomer" via Equation 5B. The "Mole Percent Comonomer" was plotted as a function of polyethylene-equivalent molecular weight, as determined using Equation 1B, as discussed above. See FIG. 6 (Log Mwi used as the x-axis). A linear fit was from Mwi of 15,000 g/mole to Mwi of 150,000 g/mole, yielding a slope of "2.27 mole percent comonomer×mole/g." Thus, the MWCDI=2.27. An EXCEL linear regression was used to calculate the slope between, and including, Mwi from 15,000 to 150,000 g/mole.

Shrink %

The shrink of a monofilament (expressed as the percentage reduction in length of a 1 meter sample of the monofilament) is measured by immersing the monofilament for 20 seconds in a bath of silicon oil maintained at 90° C. Shrinkage is then calculated as: (length before−length after)/length before*100%.

Curl

Curl is measured by taking a bundle of 20 filaments and leaving it for 10 minutes in an oven at 90° C. The classification is made visually by ranking the samples based on a catalogue of standard samples. The method looks at how much the originally straight filaments tend to bend and curl on the sides. The samples are ranked between 1-5, with 1 representing filaments that showed no or very minor bending and curling and 5 representing filaments showing strong bending and curling.

Basis Weight

The basis weight of filaments is typically reported in the industry by the dTex value. The dTex of a monofilament is equal to the weight in grams of 10 km of the monofilament.

EXAMPLES

The following examples illustrate the present invention, but are not intended to limit the scope of the invention.

Example 1

Inventive First Compositions 1, 2 and 3

Inventive first compositions 1, 2 and 3, each contain two ethylene-octene copolymers. Each composition was prepared, via solution polymerization, in a dual series loop reactor system according to U.S. Pat. No. 5,977,251 (see FIG. 2 of this patent), in the presence of a first catalyst system, as described below, in the first reactor, and a second catalyst system, as described below, in the second reactor.

The first catalyst system comprised a bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula (CAT 1):

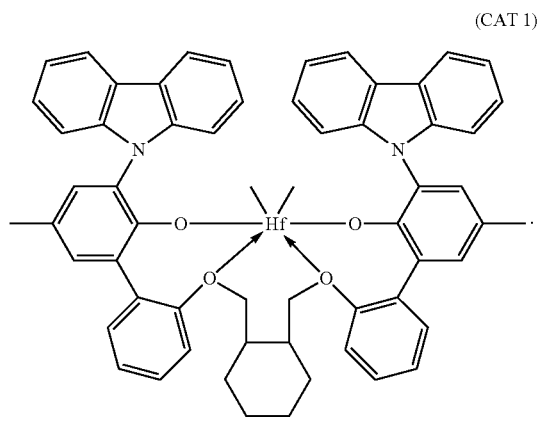

(CAT 1)

The molar ratios of the metal of CAT 1, added to the polymerization reactor, in-situ, to that of Cocat1 (modified methyl aluminoxane), or Cocat2 (bis(hydrogenated tallow alkyl)methyl, tetrakis(pentafluorophenyl)borate(1-) amine), are shown in Table 1.

The second catalyst system comprised a Ziegler-Natta type catalyst (CAT 2). The heterogeneous Ziegler-Natta type catalyst-premix was prepared substantially according to U.S. Pat. No. 4,612,300, by sequentially adding to a volume of ISOPAR E, a slurry of anhydrous magnesium chloride in ISOPAR E, a solution of EtAlCl$_2$ in heptane, and a solution of Ti(O-iPr)$_4$ in heptane, to yield a composition containing a magnesium concentration of 0.20M, and a ratio of Mg/Al/Ti of 40/12.5/3. An aliquot of this composition was further diluted with ISOPAR-E to yield a final concentration of 500 ppm Ti in the slurry. While being fed to, and prior to entry into, the polymerization reactor, the catalyst premix was contacted with a dilute solution of Et$_3$Al, in themolar Al to Ti ratio specified in Table 1, to give the active catalyst.

Figure 7:
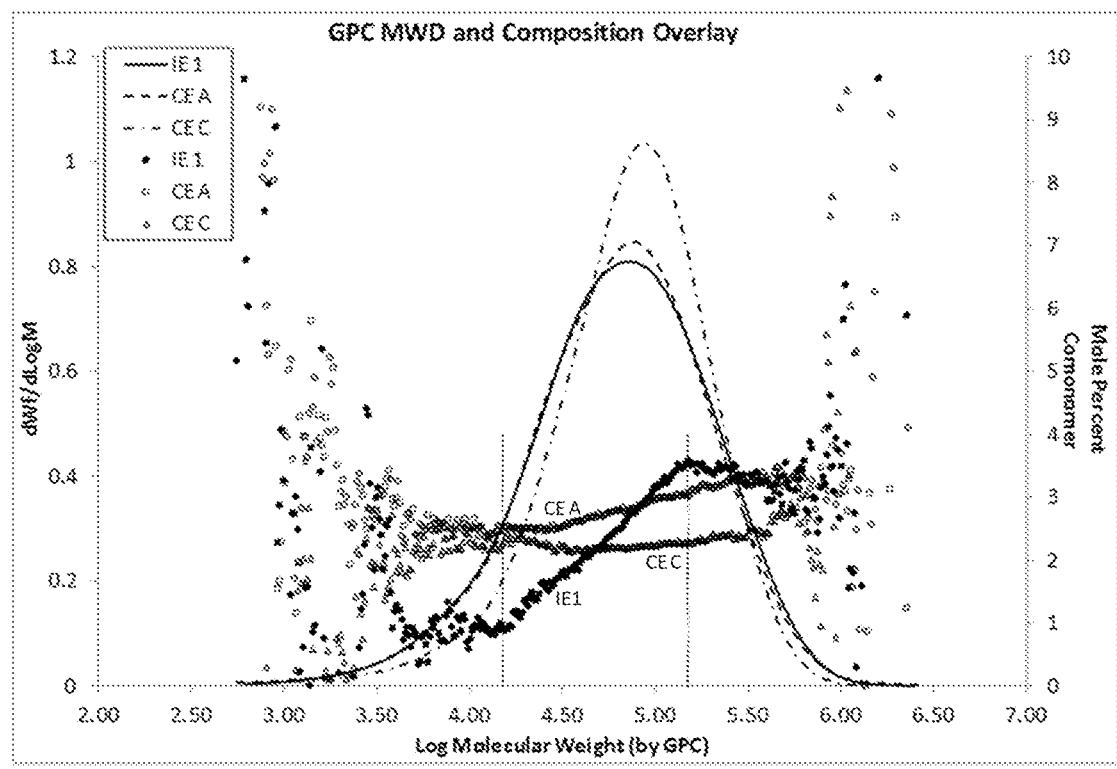
FIG. 7 depicts some GPC MWD profiles and corresponding comonomer distribution overlays for some inventive and comparative compositions (density 0.916-0.919 g/cc).
Figure 8:
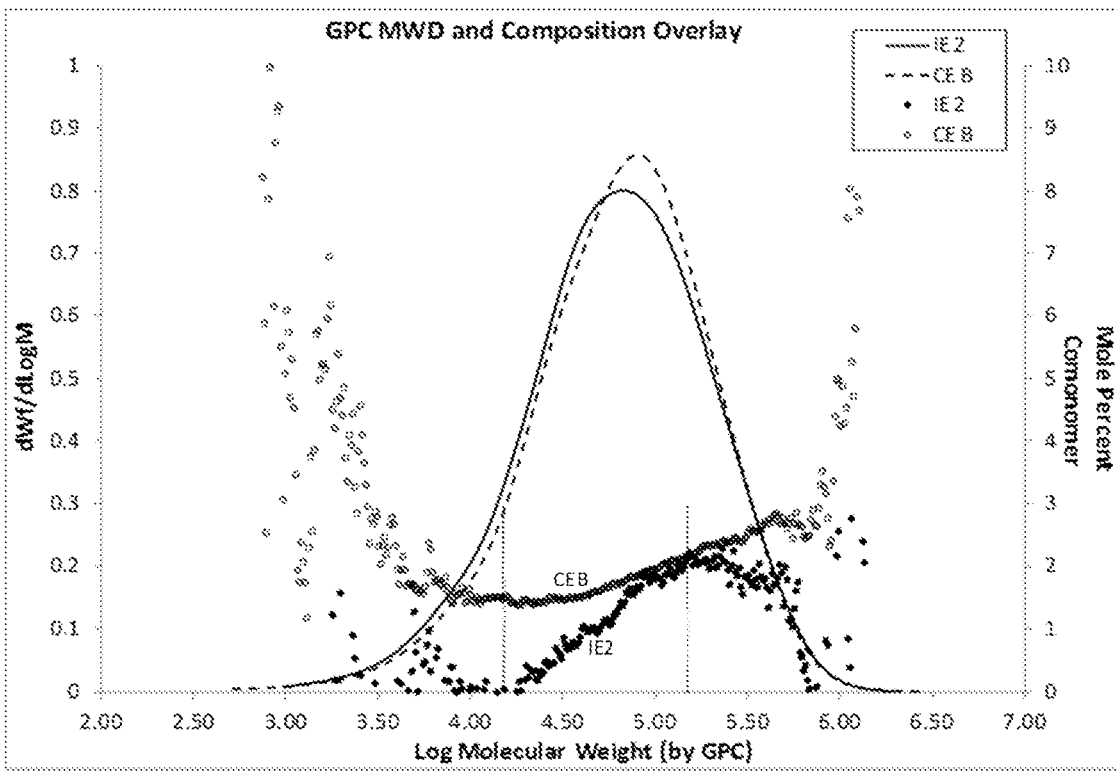
FIG. 8 depicts some GPC MWD profiles and corresponding comonomer distribution overlays for some inventive and comparative compositions (density 0.924-0.926 g/cc).
Figure 9:
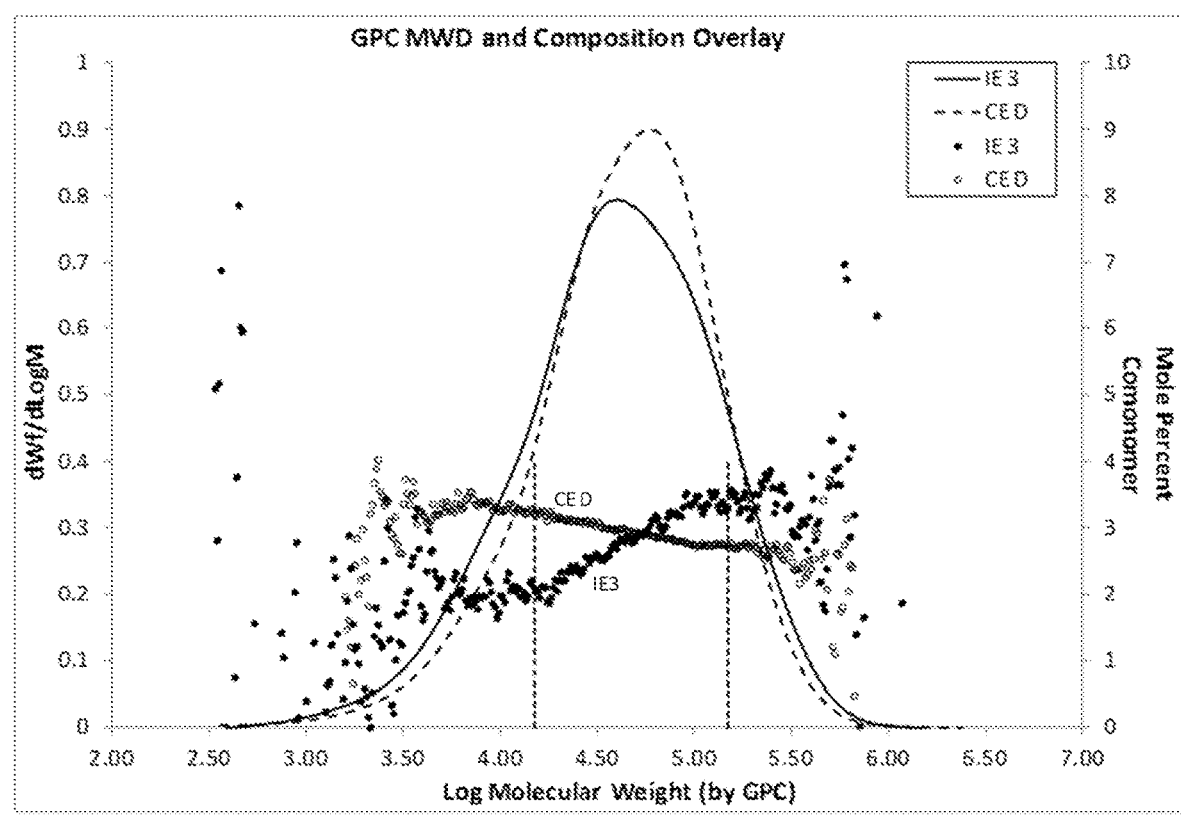
FIG. 9 depicts some GPC MWD profiles and corresponding comonomer distribution overlays for some inventive and comparative compositions (Cast stretch).

The polymerization conditions for the inventive first compositions 1, 2 and 3 are reported in Table 1. As seen in Table 1, Cocat. 1 (modified methyl aluminoxane (MMAO)); and Cocat. 2 (bis(hydrogenated tallow alkyl)methyl, tetrakis(pentafluorophenyl)borate(1-) amine) were each used as a cocatalyst for CAT 1. Additional properties of the inventive compositions 1, 2 and 3 were measured, and are reported in Table 2. The GPC MWD profiles, and corresponding comonomer distribution overlays, are shown in FIGS. 7-9. Each polymer composition was stabilized with minor (ppm) amounts of stabilizers.

Comparative First Compositions A and B

Comparative compositions A and B, each contain two ethylene-octene copolymers, and each was prepared, via solution polymerization, in a dual loop reactor system, in the presence of a first catalyst system, as described below, in the first reactor, and a second catalyst system, as described below, in the second reactor. The first catalyst system comprised titanium, [N-(1,1-dimethylethyl)-1,1-dimethyl-1-[(1,2,3,3a,8a-η)-1,5,6,7-tetrahydro-2-methyl-s-indacen-1-yl]silanaminato(2-)-κN][(1,2,3,4-η)-1,3-pentadiene]-(CAT 3, a constrained geometry catalyst). The second catalyst system comprised the Ziegler-Natta premix (CAT 2), as discussed above.

The polymerization conditions for comparative compositions A and B are reported in Table 1. As seen in Table 1, Cocat. 1 (modified methyl aluminoxane (MMAO)) and Cocat. 2 (bis(hydrogenated tallow alkyl)methyl, tetrakis(pentafluorophenyl)borate(1-) amine) were each used as cocatalysts for CAT 3. Additional properties of the comparative compositions A and B were measured, and are reported in Table 2. The GPC MWD profiles, and corresponding comonomer distribution overlays, are shown in FIGS. 7 and 8. Each polymer composition was stabilized with minor (ppm) amounts of stabilizers.

Comparative C (First Composition)

Comparative C is an ethylene-hexene copolymer composition, commercially available under the commercial designation EXCEED 1018CA from EXXONMOBIL Chemical Company, and having a density of approximately 0.918 g/cm$^3$, a melt index (I$_2$ or I2), measured at 190° C. and 2.16 kg, of approximately 1.0 g/10 minutes. Additional properties of the comparative example C were measured, and are reported in Table 2. The GPC MWD profile, and corresponding comonomer distribution overlay, is shown in FIG. 7.

Comparative D (First Composition)

Comparative D is an ethylene-octene copolymer composition, provided by The Dow Chemical Company, under the commercial designation ELITE 5230G, and having a density of approximately 0.916 g/cm³, a melt index (I₂ or I2), measured at 190° C. and 2.16 kg, of approximately 4.0 g/10 minutes. Additional properties of the comparative example D were measured, and are reported in Table 2. The GPC MWD profile, and corresponding comonomer distribution overlay, is shown in FIG. 9.

TABLE 1

Polymerization Conditions (Rx1 = reactor 1; Rx2 = reactor 2)

| | Units | Inv. First 1 | Inv. First 2 | Inv. First 3 | Comp. First A | Comp. First B |
|---|---|---|---|---|---|---|
| Reactor Configuration | | Dual Series | Dual Series | Dual Series | Dual Series | Dual Series |
| Comonomer | | 1-octene | 1-octene | 1-octene | 1-octene | 1-octene |
| REACTOR FEEDS | | | | | | |
| First Reactor Total Solvent Flow | lb/hr | 1122 | 1057 | 1177 | 958 | 1061 |
| First Reactor Total Ethylene Flow | lb/hr | 190 | 175 | 269 | 184 | 187 |
| First Reactor Total Comonomer Flow | lb/hr | 74 | 48 | 118 | 97 | 58 |
| First Reactor Hydrogen Feed Flow | SCCM | 6827 | 5017 | 22848 | 525 | 857 |
| Second Reactor Total Solvent Flow | lb/hr | 384 | 451 | 421 | 494 | 561 |
| Second Reactor Total Ethylene Flow | lb/hr | 173 | 204 | 155 | 182 | 216 |
| Second Reactor Total Comonomer Flow | lb/hr | 12 | 8 | 22 | 50 | 17 |
| Second Reactor Hydrogen Feed Flow | SCCM | 298 | 99 | 100 | 2446 | 3829 |
| REACTION | | | | | | |
| First Reactor Control Temperature | ° C. | 140 | 150 | 143 | 145 | 135 |
| First Reactor Ethylene Conversion | % | 86.7 | 90.5 | 72.7 | 69.4 | 77.7 |
| First Reactor Viscosity | cP | 2400 | 2315 | 824 | 891 | 1318 |
| Second Reactor Control Temperature | ° C. | 195 | 195 | 190 | 190 | 195 |
| Second Reactor Ethylene Conversion | % | 87.1 | 86 | 87.8 | 89.2 | 88.8 |
| Second Reactor Viscosity | cP | 869 | 876 | 264 | 892 | 848 |
| CATALYST | | | | | | |
| First Reactor Catalyst | type | CAT 1 | CAT 1 | CAT 1 | CAT 3 | CAT 3 |
| First Reactor Catalyst Efficiency | g polymer per g catalyst metal | 3,681,068 | 2,333,579 | 481,051 | 2,984,071 | 2,653,724 |
| First Reactor Cocatalyst (Cocat. 2) to Catalyst Metal Molar Ratio | Ratio | 1.3 | 1.8 | 1.2 | 1.2 | 1.5 |
| First Reactor Cocatalyst (Cocat. 1) to Catalyst Metal Molar Ratio | Ratio | 20 | 100 | 5 | 15 | 25 |
| Second Reactor Catalyst Efficiency | g polymer per g catalyst metal | 404,385 | 469,511 | 176,500 | 561,063 | 390,994 |
| Second Reactor Al to Ti Molar Ratio | Ratio | 4.0 | 4.0 | 1.2 | 4.0 | 4.0 |

*solvent = ISOPAR E

TABLE 2

Properties of Inventive and Comparative Compositions

| | Unit | Inv. First 1 | Inv. First 2 | Inv. First 3 | Comp. First A | Comp. First B | Comp. First C | Comp. First D |
|---|---|---|---|---|---|---|---|---|
| Density | g/cc | 0.9174 | 0.9245 | 0.9148 | 0.9162 | 0.9253 | 0.9191 | 0.9158 |
| $I_2$ | g/10 min | 0.83 | 0.87 | 3.91 | 0.93 | 0.80 | 0.95 | 4.05 |
| $I_{10}/I_2$ | | 7.7 | 8.0 | 7.3 | 8.2 | 8.4 | 6.0 | 7.0 |
| $7.0 - 1.2 \times \log(I2)$ | | 7.1 | 7.1 | 6.3 | 7.0 | 7.1 | 7.0 | 6.3 |

TABLE 2-continued

Properties of Inventive and Comparative Compositions

|  | Unit | Inv. First 1 | Inv. First 2 | Inv. First 3 | Comp. First A | Comp. First B | Comp. First C | Comp. First D |
|---|---|---|---|---|---|---|---|---|
| Mn (conv.gpc) | g/mol | 32,973 | 33,580 | 20,244 | 33,950 | 34,626 | 45,645 | 26,355 |
| Mw (conv.gpc) |  | 117,553 | 117,172 | 78,820 | 111,621 | 112,688 | 109,931 | 76,118 |
| Mz (conv.gpc) |  | 270,191 | 277,755 | 186,520 | 258,547 | 254,301 | 197,425 | 155,254 |
| Mw/Mn (conv.gpc) |  | 3.57 | 3.49 | 3.89 | 3.29 | 3.25 | 2.41 | 2.89 |
| Mz/Mw (conv.gpc) |  | 2.30 | 2.37 | 2.37 | 2.32 | 2.26 | 1.80 | 2.04 |
| Eta* (0.1 rad/s) | Pa · s | 9,496 | 11,231 | 1,997 | 10,342 | 11,929 | 6,975 | 2,057 |
| Eta* (1.0 rad/s) | Pa · s | 7,693 | 8,455 | 1,920 | 7,313 | 7,942 | 6,472 | 1,908 |
| Eta* (10 rad/s) | Pa · s | 4,706 | 4,977 | 1,527 | 4,337 | 4,586 | 5,071 | 1,473 |
| Eta* (100 rad/s) | Pa · s | 1,778 | 1,893 | 792 | 1,769 | 1,873 | 2,415 | 834 |
| Eta*0.1/Eta*100 |  | 5.34 | 5.93 | 2.52 | 5.85 | 6.37 | 2.89 | 2.47 |
| Eta zero | Pa · s | 11,210 | 13,947 | 2,142 | 12,994 | 15,661 | 7,748 | 2,176 |
| MWCDI |  | 2.64 | 2.27 | 1.56 | 0.65 | 0.79 | −0.06 | −0.54 |
| Vinyls | Per 1000 total Carbons | 134 | 179 | 115 | 157 | 148 | 69 | 56 |
| ZSVR |  | 1.53 | 1.92 | 1.25 | 2.13 | 2.49 | 1.35 | 1.45 |

Example 2

Inventive Compositions 4 and 5

Inventive compositions 4 and 5 each contain an ethylene-octene copolymer. Inventive compositions 4 and 5 were prepared in the same manner and using the same catalyst system as inventive compositions 1-3, with the exception of the polymerization conditions which are reported in Table 3.

TABLE 3

Polymerization Conditions (Rx1 = reactor 1; Rx2 = reactor 2)

| Sample # | Units | Inv. Comp. 4 | Inv. Comp. 5 |
|---|---|---|---|
| Reactor Configuration |  | Dual Series | Dual Series |
| Comonomer |  | 1-octene | 1-octene |
| REACTOR FEEDS |  |  |  |
| First Reactor Total Solvent Flow | lb/hr | 1323 | 957 |
| First Reactor Total Ethylene Flow | lb/hr | 228 | 200 |
| First Reactor Total Comonomer Flow | lb/hr | 86 | 71 |
| First Reactor Hydrogen Feed Flow | SCCM | 6379 | 4578 |
| Second Reactor Total Solvent Flow | lb/hr | 525 | 464 |
| Second Reactor Total Ethylene Flow | lb/hr | 201 | 211 |
| Second Reactor Total Comonomer Flow | lb/hr | 12 | 13 |
| Second Reactor Hydrogen Feed Flow | SCCM | 4392 | 2233 |
| REACTION |  |  |  |
| First Reactor Control Temperature | ° C. | 165 | 165 |
| First Reactor Ethylene Conversion | % | 89.0 | 92.0 |
| First Reactor Viscosity | cP | 402 | 1121 |
| Second Reactor Control Temperature | ° C. | 195 | 195 |
| Second Reactor Ethylene Conversion | % | 86.2 | 84.7 |
| Second Reactor Viscosity | cP | 219 | 524.7 |
| CATALYST |  |  |  |
| First Reactor Catalyst | type | CAT 1 | CAT 1 |
| First Reactor Catalyst Efficiency | g polymer per g catalyst metal | 617060 | 1204000 |
| First Reactor Cocatalyst (Cocat. 2) to Catalyst Metal Molar Ratio | Ratio | 1.2 | 1.2 |
| First Reactor Cocatalyst (Cocat. 1) to Catalyst Metal Molar Ratio | Ratio | 18.0 | 50.0 |
| Second Reactor Catalyst Efficiency | g polymer per g catalyst metal | 354157 | 422627 |
| Second Reactor Al to Ti Molar Ratio | Ratio | 4.0 | 4.0 |

*solvent = ISOPAR E

Comparative Composition E

Comparative composition E is an ethylene-octene copolymer composition, commercially available under the commercial designation DOWLEX™ 2107GC from the Dow Chemical Company, and having a density of approximately 0.917 g/cm$^3$ and a melt index ($I_2$ or I2), measured at 190° C. and 2.16 kg, of approximately 2.3 g/10 minutes. Additional properties of the comparative composition E were measured, and are reported in Table 4.

TABLE 4

Properties of Inventive and Comparative Compositions

|  | Unit | Inv. Comp. 4 | Inv. Comp. 5 | Comp. Comp. E |
|---|---|---|---|---|
| Density | g/cc | 0.9178 | 0.9179 | 0.9170 |
| $I_2$ | g/10 min | 2.67 | 2.46 | 2.30 |
| $I_{10}/I_2$ |  | 8.0 | 7.6 | 7.5 |
| 7.0 − 1.2 × log(I2) |  | 6.5 | 6.5 | 6.6 |
| Mn (conv.gpc) | g/mol | 26,671 | 26,530 | 24,520 |
| Mw (conv.gpc) | g/mol | 85,484 | 91,824 | 93,283 |
| Mz (conv.gpc) | g/mol | 192,362 | 235,109 | 271,093 |
| Mw/Mn (conv.gpc) |  | 3.21 | 3.46 | 3.80 |
| Mz/Mw (conv.gpc) |  | 2.25 | 2.56 | 2.91 |

TABLE 4-continued

Properties of Inventive and Comparative Compositions

|  | Unit | Inv. Comp. 4 | Inv. Comp. 5 | Comp. Comp. E |
|---|---|---|---|---|
| Eta* (0.1 rad/s) | Pa · s | 3,148 | 3,405 | 3,606 |
| Eta* (1.0 rad/s) | Pa · s | 2,743 | 2,995 | 3,134 |
| Eta* (10 rad/s) | Pa · s | 1,911 | 2,117 | 2,181 |
| Eta* (100 rad/s) | Pa · s | 915 | 1,032 | 1,007 |
| Eta*0.1/Eta*100 |  | 3.44 | 3.30 | 3.58 |
| MWCDI |  | 0.92 | 1.97 | −0.93 |

Artificial Turf Filaments

Inventive and comparative artificial turf monofilaments are prepared from Inventive Composition 4 and from Comparative Composition E. The inventive monofilament formulation comprises 94 wt. % of Inventive Composition 4 (or Inventive Composition 5), 5 wt. % color masterbatch BASF Sicolen 85125345, and 1 wt. % processing aid Argus ARX-741. The comparative monofilament formulation comprises 94 wt. % of Comparative Composition E, 5 wt. % color masterbatch BASF Sicolen 85125345, and 1 wt. % processing aid Argus ARX-741. The additives were blended with the polymer compositions prior to extrusion. Each of the monofilaments was prepared on an extrusion line from Oerlikon Barmag (Remscheid, Germany) (see FIG. 1) as described herein.

Table 5 and FIG. 1 provide specific conditions of the equipment used in preparing the inventive and comparative monofilaments.

TABLE 5

Equipment Conditions

| Parameter | Value |
|---|---|
| Die type | Mexican Hat (total 48 holes) |
| Extruder Temperature | melt T 230° C. |
| Distance die-to-water bath (see FIG. 1) | 40 mm |
| Temperature water bath | 35° C. |
| Temperature stretching oven | 97° C. |
| Temperature annealing ovens | Oven 1: 118° C. |
|  | Oven 2: 118° C. |
|  | Oven 3: 115° C. |
| Final speed - V5 (FIG. 1) | 200 m/min |

The inventive and comparative monofilaments were tested for tenacity, elongation, shrinkage and curl. Tenacity and elongation were measured on a Zwick tensile tester on a filament length of 250 mm and extension rate of 250 mm/min until the filament breaks. Tenacity is defined as the tensile force at break divided by the linear weight (dtex). Elongation is the strain at break. Three samples are measured and the average values are calculated. The results are shown in Table 6.

TABLE 6

Monofilament Test Results

| Property | Unit | Inv. Fil. 4 | Comp. Fil. E |
|---|---|---|---|
| Tenacity | cN/dtex | 0.93 | 0.91 |
| Elongation | % | 51.9 | 40.6 |
| Shrink | % | 5.8 | 8.8 |
| Curl |  | 1.0 | 2.0 |

As shown in Table 6, the artificial turf filaments formed from Inventive Composition 4 exhibit improved properties for artificial turf applications than the artificial turf filament formed from Comparative Composition E. Specifically, the artificial turf filaments formed from Inventive Composition 4 have higher tenacity and elongation, as well as lower Shrink and Curl than the artificial turf filaments formed from Comparative Composition E.

That which is claimed:

1. An artificial turf filament comprising a first composition, wherein the first composition comprises at least one ethylene-based polymer comprising ethylene and at least one polymerized comonomer, and wherein the first composition comprises a Molecular Weighted Comonomer Distribution Index (MWCDI) value greater than 1.2, and a melt index ratio (I10/I2) that meets the following equation: I10/I2≥7.0−1.2×log (I2).

2. The artificial turf filament of claim 1, wherein the first composition has a MWCDI value less than, or equal to, 10.0.

3. The artificial turf filament of claim 1, wherein the first composition has a density of 0.905 to 0.940 g/cm³ and a melt index (I2) of 0.5 to 5 g/10 minutes.

4. The artificial turf filament of claim 1, wherein the filament exhibits a shrink of less than 6%.

5. The artificial turf filament of claim 1, wherein the filament exhibits an elongation of 40% or more.

6. The artificial turf filament of claim 1, wherein the first composition has a ZSVR value from 1.2 to 2.0.

7. A method of manufacturing an artificial turf filament, the method comprising:
providing a first composition, wherein the first composition comprises at least one ethylene-based polymer comprising ethylene and at least one polymerized comonomer, and wherein the first composition comprises a Molecular Weighted Comonomer Distribution Index (MWCDI) value greater than 1.2, and a melt index ratio (I10/I2) that meets the following equation: I10/I2≥7.0−1.2×log (I2); and
extruding the first composition into an artificial turf filament.

8. The method of claim 7, wherein the method further comprises stretching the artificial turf filament to a predetermined stretch ratio.

9. The method of claim 8, wherein the stretch ratio is at least 4.

10. An artificial turf comprising:
a primary backing having a top side and a bottom side; and
at least one artificial turf filament according to claim 1;
wherein the at least one artificial turf filament is affixed to the primary backing such that the at least one artificial turf filament provides a tufted face extending outwardly from the top side of the primary backing.

11. The artificial turf of claim 10, wherein the artificial turf further comprises a secondary backing bonded to at least a portion of the bottom side of the primary backing such that the at least one artificial turf filament is affixed in place to the bottom side of the primary backing.

12. A method of manufacturing an artificial turf, the method comprising:
- providing at least one artificial turf filament according to claim 1; and
- affixing the at least one artificial turf filament to a primary backing such that that at least one artificial turf filament provides a tufted face extending outwardly from a top side of the primary backing.

13. The method of claim 12, wherein the method further comprises bonding a secondary backing to at least a portion of the bottom side of the primary backing such that the at least one artificial turf filament is affixed in place to the bottom side of the primary backing.

* * * * *